United States Patent
Brentano et al.

(10) Patent No.: US 7,094,541 B2
(45) Date of Patent: Aug. 22, 2006

(54) ASSAY FOR DETECTION OF HUMAN PARVOVIRUS B19 NUCLEIC ACID

(75) Inventors: Steven T. Brentano, Santee, CA (US); Margarita Batranina-Kaminsky, San Diego, CA (US); Cynthia S. Hasselkus-Light, San Diego, CA (US); Daniel P. Kolk, Ramona, CA (US)

(73) Assignee: Gen-Probe Incorporated, San Diego, CA (US)

( * ) Notice: Subject to any disclaimer, the term of this patent is extended or adjusted under 35 U.S.C. 154(b) by 463 days.

(21) Appl. No.: 10/231,843

(22) Filed: Aug. 30, 2002

(65) Prior Publication Data

US 2003/0124578 A1 Jul. 3, 2003

Related U.S. Application Data

(60) Provisional application No. 60/316,691, filed on Aug. 31, 2001.

(51) Int. Cl.
*C12Q 1/68* (2006.01)
*C12P 19/34* (2006.01)
*C07H 21/04* (2006.01)

(52) U.S. Cl. .................. 435/6; 435/91.1; 435/91.2; 536/23.1; 536/24.3; 536/24.32

(58) Field of Classification Search .................. None
See application file for complete search history.

(56) References Cited

U.S. PATENT DOCUMENTS

| | | | |
|---|---|---|---|
| 5,399,491 A * | 3/1995 | Kacian et al. | 435/91.21 |
| 5,449,608 A | 9/1995 | Young et al. | |
| 5,688,669 A | 11/1997 | Murtagh | |
| 5,744,306 A | 4/1998 | Murtagh, Jr. et al. | |
| 5,853,733 A | 12/1998 | Cochran et al. | |
| 6,183,999 B1 | 2/2001 | Weimer et al. | |
| 6,214,555 B1 * | 4/2001 | Leushner et al. | 435/6 |
| 6,322,795 B1 | 11/2001 | Shamanin et al. | |
| 6,642,033 B1 | 11/2003 | Lazo et al. | |

FOREIGN PATENT DOCUMENTS

| | | |
|---|---|---|
| JP | 04088985 A | 3/1992 |
| WO | WO 91/12269 A1 | 8/1991 |
| WO | WO 96/09391 A2 | 3/1996 |
| WO | WO 96/27799 A1 | 9/1996 |
| WO | WO 97/41257 A1 | 11/1997 |
| WO | WO 98/42847 A2 | 10/1998 |
| WO | WO98/50583 | 11/1998 |
| WO | WO 99/28439 * | 6/1999 ..... 435/6 |
| WO | WO 99/28439 A2 | 6/1999 |
| WO | WO 99/43362 A1 | 9/1999 |
| WO | WO01/04361 A2 | 1/2001 |
| WO | WO 01/06019 A2 | 1/2001 |
| WO | WO 01/14593 A2 | 3/2001 |
| WO | WO 01/96612 A2 | 12/2001 |
| WO | WO 02/00924 A2 | 1/2002 |
| WO | WO03/002753 A2 | 1/2003 |

OTHER PUBLICATIONS

Takahashi et al., May 1999, FEBS Letter, vol. 450, pp. 289-291.*
Results 27-34 of SEQ ID No.: 13 search in GenEmbl database.*
Results 17-24 of SEQ ID No.: 24 search in GenEmbl database.*
Result 3 of SEQ ID No.: 33 search in Geneseq database.*
Durigon et al., Oct. 1993, J. Virological Methods, vol. 44, pp. 156, 158 and 159.*
GenBank accession numbers AB015954, AB015955, AB015956, AB015957, AB015958, AB015960, AB018642, AB018643.*
Tereshko, Jul. 1998, Biochemistry, vol. 37, p. 10627.*
Bostic et al., "Quantitative analysis of neutralizing immune response to human parvovirus B19 using a novel reverse transcriptase-polymerase chain reaction-based assay", J. Infect. Dis., Mar. 1999, vol. 179, No. 3, pp. 619-626.
Brown et al., "Parvovirus B19 in Human Disease", Ann. Rev. Med., 1997, vol. 48, pp. 59-67.
Carriere et al., "Rapid and sensitive method for the detection of B19 virus DNA using the polymerase chain reaction with nested primers", J. Virol. Meth., Oct. 1993, vol. 44, Nos. 2-3, pp. 221-234.
Cassinotti et al., "Human parvovirus B19 infections: Routine diagnosis by a new nested polymerase chain reaction assay", J. Med. Virol., Jul. 1993, vol. 40, No. 3, pp. 228-234.
Clewley, J.P., "Polymerase chain reaction assay for parvovirus B19 DNA in clinical specimens", J. Clin. Microbiol., Dec. 1989, vol. 27, No. 12, pp. 2647-2651.
Cotmore et al., "Identification of the major structural and nonstructural proteins encoded by human parvovirus B19 and mapping of their genes by procaryotic expression of isolated genomic fragments", J. Virol., Nov. 1986, vol. 60, No. 2, pp. 548-557.
Cubie et al., "Dot-blot hybridisation assay for detection of parvovirus B19 infections using synthetic oligonucleotides", Mol. Cell. Probes, Feb. 1995, vol. 9, No. 1, pp. 59-66.
Durigon et al., "Multiple primer pairs for polymerase chain reaction (PCR) amplification for human parvovirus B19 DNA", J. Virol. Meth., Oct. 1993, vol. 44, Nos. 2-3, pp. 155-165.
Fini et al., "Development of a chemiluminescence competition PCR for the detection and quantificatiion of parvovirus B19 DNA using a microtitre luminometer", Clin. Chem., Sep. 1999, vol. 45, No. 9, pp. 1391-1396.
Frickhofen et al., "A rapid method to sample preparation for detection of DNA viruses in human serum by polymerase chain reaction", J. Virol. Meth., Nov. 1991, vol. 35, No. 1, pp. 65-72.
Gallinella et al., "In situ hybridization and in situ polymerase chain reaction detection of parvovirus B19 DNA within cells", J. Virol. Meth., Dec. 1994, vol. 50, Nos. 1-3, pp. 67-74.

(Continued)

Primary Examiner—Jehanne Sitton
(74) Attorney, Agent, or Firm—Christine A. Gritzmacher

(57) ABSTRACT

Nucleic acid oligomers specific for human parvovirus B19 genomic DNA are disclosed. An assay for amplifying and detecting human parvovirus B19 nucleic acid in biological specimens is disclosed. Compositions for detecting the presence of parvovirus B19 genomic DNA in human biological specimens are disclosed.

25 Claims, No Drawings

OTHER PUBLICATIONS

Gruber et al., "Precise quantitation of human parvovirus B19 DNA in biological samples by PCR", Biologicals, Sep. 1998, vol. 26, No. 3, pp. 213-216.

Hokynar et al., "Integrity and full coding sequence of B19 virus DNA persisting in human synovial tissue", J. Gen, Virol., Apr. 2000, vol. 81, Pt. 4, pp. 1017-1025.

Hornsleth et al., "Estimation of serum concentration of parvovirus B19 DNA by PCR in patients with chronic anaemia", Res. Virol., Nov.-Dec. 1994, vol. 145, No. 6, pp. 379-386.

Koch et al., "Detection of human parvovirus B19 DNA by using the polymerase chain reaction", J. Clin. Microbiol., Jan. 1990, vol. 28, No. 1, pp. 65-69.

McOmish et al., "Detection of parvovirus B19 in donated blood: a model system for screening by polymerase chain reaction", J. Clin. Microbiol., Feb. 1993, vol. 31, No. 2, pp. 323-328.

Mori et al., "Dot blot hybridization assay of B19 Virus DNA in clinical samples" J. Clin. Microbiol., Mar. 1989, vol. 27, No. 3, pp. 459-464.

Musiani et al., "Nested polymerase chain reaction assay for the detection of B19 parvovirus DNA in human immunodeficiency virus patients", J. Med. Virol., Jun. 1993, vol. 40, No. 2, pp. 157-160.

Patou et al., "Characterization of a nested polymerase chain reaction assay for detection of parvovirus B19", J. Clin. Microbiol., Mar. 1993, vol. 31, No. 3, pp. 540-546.

Prowse et al., "Human parvovirus B19 and blood products", Vox Sanguinis, 1997, vol. 72, No. 1, pp. 1-10.

Rogers et al., "Detection of human parvovirus B19 in early spontaneous abortuses using serology, histology, electron microscopy, in situ hybridization, and the polymerase chain reaction", Obstet. Gynecol., Mar. 1993, vol. 81, No. 3, pp. 402-408.

Salimans et al., "Rapid detection of human parvovirus B19 DNA by dot-hybridization and the polymerase chain reaction", J. Virol. Meth., Jan. 1989, vol. 23, No. 1, pp. 19-28.

Sato et al., "Development of a hypersensitive detection method for human parvovirus B19 DNA", J. Clin. Microbiol., Mar. 2000, vol. 38, No. 3, p. 1241-3.

Schowengerdt et al., "Association of parvovirus B19 genome in children with myocarditis and cardiac allograft rejection", Circulation, Nov. 1997, vol. 96, No. 10, pp. 3549-3554.

Sevall, J.S., "Detection of parvovirus B19 by dot-blot and polymerase chain reaction", Mol. Cell. Probes, Jun. 1990, vol. 4, No. 3, pp. 237-246.

Shade et al., "Nucleotide sequence and genome organization of human parvovirus B19 isolated from the serum of a child during aplastic crisis", J. Virol., Jun. 1986, Vol. 58, No. 3, pp. 921-936.

Shyamala et al., "Detection of parvovirus B19 in human plasma samples by nucleic acid amplification technologies (NAT)", Abstract SP170, Transfusion, Sep. 2001 vol. 41, No. 9S, Suppl., pp. 86S.

Wattre et al., "A clinical and epidemiological study of human parvovirus B19 infection in fetal hydrops using PCR Southern blot hybridization and chemiluminescence detection", J. Med. Virol., Feb. 1998, vol. 54, No. 2, pp. 140-144.

Yamakawa et al., "Detection of human parvovirus B19 DNA by nested polymerase chain reaction", Obstet. Gynecol., Jul. 1995, vol. 86, No. 1, pp. 126-129.

Yoto et al., "Large-scale screening for human parvovirus B19 DNA in clinical specimens by dot blot hybridization and polymerase chain reaction", J. Med. Virol., Dec. 1995, vol. 47, No. 4, pp. 438-441.

Zakrzewska et al., "Polymerase chain reaction for synthesis of digoxigenin-labelled DNA probe: application to parvovirus B19 and to polyomavirus BK", Mol. Cell. Probes, Feb. 1993, Vol. 7, No 1, pp. 55-60.

Umene et al., "Genetic Diversity of Human Parvovirus B19 Determined Using a Set of Restriction Endonucleases Recognizing Four or Five Base Palrs and Partial Nucleotide Sequencing: Use of Sequence Variability in Virus Classification", J. Gen. Virol., Aug. 1991, 72(Pt. 8):1997-2001.

Aberhan et al., "A quantitative, Internally controlled real-time PCR assay for the detection of parvovirus B19 DNA", J. Virol. Meth., Apr. 2001, vol. 92, No. 2, pp. 183-191.

Johansen et al., "Typing of European strains of parvovirus B19 by restriction ondonucloaso analysis and sequencing: Identification of evolutionary lineages and evidence of recombination of markers from different lineages", Virus Res., Feb. 1998, vol. 53, No. 2, pp. 215-223.

Lefrere et al., "Albumin batches and B19 parvovirus DNA", Transfusion, May 1995, vol. 35, No. 5, pp. 389-391.

Diss et al., "Parvovirus B19 is associated with benign testes as well as testicular germ cell tumours", J. Clin. Pathol.: Mol. Pathol, Dec. 1999, vol. 52, No. 6, pp. 349-352.

Database GenEmbl, Accession No. Z70533, HEMAUER et al "Parvovirus B19 DNA, patient 3, genome position 2647-2938," Nov. 1996.

Database GenEmbl, Accession No. Z70591, HEMAUER et al "Parvovirus B19 DNA, patient S724, genome position 2448-2977," Apr. 1996.

Database GenEmbl, Accession No. AF380251, Sol-Church et al., "B19 virus Isolate 7 VP1 protein gene, partial cds," Jun. 2001.

Stringfellow et al., "Simultaneous Detection of Parvovirus B19 and Hepatitis A Virus (HAV) in Human Plasma Using a Transcription-Mediated Amplification (TMA) Assay", Vox Sanguinis, vol. 83, Suppl. 2, p. 184, Aug. 2002, XP0090474238 (*Abstract* P-553).

\* cited by examiner

ASSAY FOR DETECTION OF HUMAN PARVOVIRUS B19 NUCLEIC ACID

RELATED APPLICATION

This application claims the benefit of U.S. provisional application No. 60/316,691, filed Aug. 31, 2001, under 35 U.S.C. 119(e).

FIELD OF THE INVENTION

This invention relates to diagnostic methods and compositions for detecting a human infectious agent, and specifically relates to methods and compositions for detecting the nucleic acid of parvovirus B19 in vitro.

BACKGROUND OF THE INVENTION

Human parvovirus B19 (sometimes called erythrovirus) is a blood borne, non-enveloped virus that has a single-stranded DNA (ssDNA) genome of about 5.5 kb (Shade et al., 1986, *J. Virol.* 58(3): 921–936, Brown et al., 1997, *Ann. Rev. Med.* 48: 59–67). Individual virions contain one copy of either the plus or minus strand of the genome, represented in approximately equal numbers. The ssDNA genome has inverted terminal repeats that form 5' and 3' hairpins of about 350 nt which are essential for viral replication. The genome includes two open reading frames on the plus strand which code for structural proteins (VP1 and VP2) and non-structural protein (NS1).

Infection with parvovirus B19 can occur via respiratory transmission or through infected blood or blood products. Viremia can reach high levels (e.g., up to $10^{11}$ per ml of blood) at about a week after inoculation, but is generally cleared within about two weeks following infection. Infected individuals may exhibit no symptoms, or have erythema infectiosum symptoms that include mild flu-like symptoms, rash, and/or temporary arthritis-like joint pain (arthropathy). Children are more likely than adults to develop the rash (called "fifth disease"), whereas arthropathy is a common symptom in adults. More serious problems occur in susceptible patients, including aplastic crisis in patients with hemolytic anemias, and persistent parvovirus infection and other hematologic changes in immunosuppressed patients. In women, parvovirus B19 infections have been associated with loss of about 10% of early pregnancies due to fetal death.

Parvovirus B19 is a relatively resistant to viral inactivation, e.g., by chemical or heat-treatment methods used to destroy infective particles in blood, serum or plasma. Also, high viral concentrations in a sample may overwhelm viral depletion methods used to remove viral contaminants from the sample. Parvovirus B19 in blood, plasma or plasma-derived products can infect additional individuals who receive contaminated transfusions or products. Plasma derivatives are often made from pooled donations (e.g., a pool of thousands of individual donations) resulting in the risk that a single contaminated donation could contaminate the pool and products derived from it. Thus, there is a need to detect the presence of human parvovirus B19 in biological samples, such as donated blood or plasma to prevent further infection. There is also a need for an assay that detects parvovirus with a sensitivity that allows detection of low titres of virus as may occur early in an infection or in diluted or pooled samples. An assay for parvovirus B19 nucleic acid which detects an appropriate level of contamination may facilitate removal of infected donated units from the blood supply or contaminated lots of pooled plasma before use.

Immunodiagnostic methods have been used to identify blood, serum or plasma that is potentially contaminated with parvovirus B19. Many methods detect anti-parvovirus antibodies (IgM or IgG) present in an individual's serum or plasma (e.g., see PCT Nos. WO 96/09391 by Wolf et al. and WO 96/27799 by Hedman et al.). Immunological methods, however, have limitations on detecting recent or current infections because they rely on detecting the body's response to the infectious agent. Because of the rapid rise in viremia following infection, an individual's blood may contain high levels of parvovirus B19 before anti-parvovirus antibodies are detectable, leading to false negative results. Because viremia is often quickly cleared, a person may remain antibody-positive even when infective particles are not present, leading to false positive results. Also, up to about 90% of adults are seropositive for parvovirus B19, making accurate immunological detection of recent or current infections difficult. Other assays detect the presence of parvovirus B19 by detecting the virus or empty viral capsid bound to a purified cellular receptor (U.S. Pat. No. 5,449,608 to Young et al.).

DNA hybridization and amplification methods have been used to detect human parvovirus B19. U.S. Pat. No. 5,688,669 to Murtagh et al. describes detection of parvovirus B19 by amplifying a 284 bp portion of parvovirus B19 DNA by using PCR and then digesting the amplified dsDNA with exonuclease to make ssDNA. The ssDNA was hybridized with two separate oligonucleotide probes, a capture probe and a detection probe, and hybrids were detected on a solid support, e.g., by using a colorimetric assay in a microtiter plate. U.S. Pat. No. 6,183,999 to Weimer et al. discloses a nucleic acid amplification assay to detect high-titer parvovirus B19 in plasma protein solutions. By amplifying DNA in the NS1 gene using suboptimal annealing and elongation temperatures, the assay is used to indicate the presence of exceptionally large amounts of pathogenic viruses in the sample. PCT No. WO 96/09391 by Wolf et al. describes cloning of the sequence that encodes the NS-1 protein by linking PCR amplified fragments. Nested PCR and/or dot-blot assays were used to detect parvovirus DNA in patients' sera, and results were correlated with symptoms and a humoral immune response to the NS-1 protein. PCT No. WO 99/28439 by Nguyen et al. discloses the genome sequence of parvovirus B19 and fragments useful as diagnostic and immunogenic agents. PCT No. WO 99/43362 by Barrett et al. discloses a quantitative test based on PCR amplification to demonstrate that plasma proteins were free of human parvovirus B19 following filtration to eliminate the pathogens. PCT No. WO 01/06019 by Lazo et al. discloses DNA oligonucleotide sequences that can hybridize to human and porcine parvovirus sequences. These oligonucleotides can serve as primers in a PCR reaction to amplify portions of the parvovirus DNA in the NS and VP regions, and as probes to detect amplified sequences. The porcine parvovirus is introduced into a sample as an internal control that is co-purified and co-amplified with the human parvovirus B19 DNA. PCT No. WO 01/14593 by Zerlauth et al. discloses a method for detecting contaminating microorganisms, such as parvovirus B19, in pooled biological samples by using two nucleic acid amplification processes that have different predetermined detection sensitivities, which is used to identify and eliminate contaminated samples. The assay first tests a screening pool made up of combined aliquots of multiple samples by using nucleic acid amplification to detect, at a first detection limit, the presence of a microorganism's nucleic acid. Next, a subpool from the positive screening pool is tested by using a second nucleic acid amplification that has a less sensitive detection limit compared to the first detection limit. An example of the method tested plasma by using PCR amplification of a fragment of parvovirus B19 DNA and detection using fluorescently-labeled probes.

PCT No. WO 02/00924 by Tijssen et al. discloses nucleic acid sequences from various parvoviruses, including human parvovirus, that contain sequences coding for viral phospholipase $A_2$ proteins or related polypeptides. These are useful for identifying agents capable of inhibiting viral phospholipase $A_2$ activity or expression, including antisense oligonucleotides, or for making improved recombinant vectors for gene therapy.

JP 04088985 by Sugamura et al. discloses a cloned gene encoding human parvovirus B19 protein VP-1, which was cloned by using PCR to amplify DNA fragments that were integrated into a cloning vector.

SUMMARY OF THE INVENTION

One aspect of the invention is a combination of at least two separate nucleic acid oligomers, wherein the oligomers are selected from the group consisting of: SEQ ID NO:4, a complementary sequence, or RNA equivalent thereof, optionally including a promoter sequence joined to a 5' terminus of the sequence, SEQ ID NO:6, a complementary sequence, or RNA equivalent thereof, optionally including a promoter sequence joined to a 5' terminus of the sequence, SEQ ID NO:8, a complementary sequence, or RNA equivalent thereof, optionally including a promoter sequence joined to a 5' terminus of the sequence, SEQ ID NO:10, a complementary sequence, or RNA equivalent thereof, optionally including a promoter sequence joined to a 5' terminus of the sequence, SEQ ID NO:12, a complementary sequence, or RNA equivalent thereof, optionally including a promoter sequence joined to a 5' terminus of the sequence, SEQ ID NO:24, a complementary sequence, or RNA equivalent thereof, optionally including a promoter sequence joined to a 5' terminus of the sequence, SEQ ID NO:26, a complementary sequence, or RNA equivalent thereof, optionally including a promoter sequence joined to a 5' terminus of the sequence, SEQ ID NO:13, a complementary sequence, or RNA equivalent thereof, SEQ ID NO:14, a complementary sequence, or RNA equivalent thereof, SEQ ID NO:15, a complementary sequence, or RNA equivalent thereof, SEQ ID NO:16, a complementary sequence, or RNA equivalent thereof, SEQ ID NO:17, a complementary sequence, or RNA equivalent thereof, optionally with a detectable label joined to the sequence, SEQ ID NO:18, a complementary sequence, or RNA equivalent thereof, optionally with a detectable label joined to the sequence, SEQ ID NO:27, a complementary sequence, or RNA equivalent thereof, optionally with a detectable label joined to the sequence, SEQ ID NO:28, a complementary sequence, or RNA equivalent thereof, optionally with a detectable label joined to the sequence, SEQ ID NO:30, a complementary sequence, or RNA equivalent thereof, optionally with a detectable label joined to the sequence, SEQ ID NO:31, a complementary sequence, or RNA equivalent thereof, optionally with a detectable label joined to the sequence, SEQ ID NO:32, a complementary sequence, or RNA equivalent thereof, optionally with a detectable label joined to the sequence, SEQ ID NO:34, a complementary sequence, or RNA equivalent thereof, optionally with a detectable label joined to the sequence, SEQ ID NO:36, a complementary sequence, or RNA equivalent thereof, optionally with a detectable label joined to the sequence, SEQ ID NO:37, a complementary sequence, or RNA equivalent thereof, optionally with a detectable label joined to the sequence, SEQ ID NO:1, a complementary sequence, or RNA equivalent thereof, and optionally a 3' tail portion that is nonspecific for a parvovirus target sequence, SEQ ID NO:2, a complementary sequence, or RNA equivalent thereof, and optionally a 3' tail portion that is nonspecific for a parvovirus target sequence, SEQ ID NO:20, a complementary sequence, or RNA equivalent thereof, and optionally a 3' tail portion that is nonspecific for a parvovirus target sequence, and SEQ ID NO:21, a complementary sequence, or RNA equivalent thereof, and optionally a 3' tail portion that is nonspecific for a parvovirus target sequence. In one embodiment, the combination is selected from the group consisting of: SEQ ID NO:13, a complementary sequence, or RNA equivalent thereof, SEQ ID NO:24, a complementary sequence, or RNA equivalent thereof, optionally including a promoter sequence joined to the 5' terminus of the sequence, SEQ ID NO:27, a complementary sequence, or RNA equivalent thereof, optionally with a detectable label joined to the sequence, and SEQ ID NO:28, a complementary sequence, or RNA equivalent thereof, optionally with a detectable label joined to the sequence. In embodiments in which the promoter sequence is joined to the 5' terminus of an oligomer sequence, a preferred promoter sequence is SEQ ID NO:19.

Another aspect of the invention is a nucleic acid oligomer consisting of a target-specific sequence contained in SEQ ID NO:29, a complementary sequence, or RNA equivalent thereof, and optionally a 3' tail portion that is nonspecific for a parvovirus target sequence. In one embodiment, the oligomer contains the target-specific sequence of SEQ ID NO:20, a complementary sequence, or RNA equivalent thereof, and optionally a 3' tail portion that is nonspecific for a parvovirus target sequence. In another embodiment, the oligomer contains the target-specific sequence of SEQ ID NO:21, a complementary sequence, or RNA equivalent thereof, and optionally a 3' tail portion that is nonspecific for a parvovirus target sequence. Yet another embodiment is an oligomer that contains the target-specific sequence of SEQ ID NO:41, a complementary sequence, or RNA equivalent thereof, and optionally a 3' tail portion that is nonspecific for a parvovirus target sequence.

One aspect of the invention is a nucleic acid oligomer consisting of a target-specific sequence of at least 25 contiguous bases contained in SEQ ID NO:1, a complementary sequence, or RNA equivalent thereof, and optionally a 3' tail portion that is nonspecific for a parvovirus target sequence.

Another aspect of the invention is a nucleic acid oligomer consisting of a sequence contained in SEQ ID NO:33, a complementary sequence, or RNA equivalent thereof. In one embodiment, the oligomer comprises a sequence consisting of SEQ ID NO:40, a complementary sequence, or RNA equivalent thereof. Another embodiment is an oligomer that contains the sequence of SEQ ID NO:32 or SEQ ID NO:28, a complementary sequence, or RNA equivalent thereof. One embodiment is the oligomer that comprises a sequence consisting of SEQ ID NO:39, a complementary sequence, or RNA equivalent thereof. In another embodiment, the oligomer contains the sequence of SEQ ID NO:30 or SEQ ID NO:31, a complementary sequence, or RNA equivalent thereof. In some embodiments, the oligomer has a backbone that includes at least one 2'-O-methoxy linkage.

Another aspect of the invention is a nucleic acid oligomer consisting of a sequence contained in SEQ ID NO:35, a complementary sequence, or RNA equivalent thereof. Embodiment include the oligomer that contains the sequence of SEQ ID NO:17, SEQ ID NO:27, or SEQ ID NO:34, or a complementary sequence, or RNA equivalent thereof. In additional embodiments, the oligomer has a backbone that includes at least one 2'-O-methoxy linkage.

Another aspect of the invention is a nucleic acid oligomer selected from the group consisting of SEQ ID NO:36, a complementary sequence, or RNA equivalent thereof, and SEQ ID NO:37, a complementary sequence, or RNA equivalent thereof. In some embodiments, the oligomer has a backbone that includes at least one 2'-O-methoxy linkage.

One aspect of the invention is a method of detecting human parvovirus B19 nucleic acid in a biological sample, comprising the steps of providing a biological sample containing parvovirus B19 nucleic acid; amplifying in vitro a portion of the parvovirus B19 nucleic acid by using at least one nucleic acid polymerase activity and at least one first amplification oligomer and one second amplification oligomer, selected from the group consisting of a first amplification oligomer of SEQ ID NO:4, SEQ ID NO:6, SEQ ID NO:8, SEQ ID NO:10, SEQ ID NO:12, SEQ ID NO:24, or SEQ ID NO:26, each optionally including a promoter sequence joined to a 5' terminus of the sequence, and a second amplification oligomer of SEQ ID NO:13, SEQ ID NO:14, SEQ ID NO:15, or SEQ ID NO:16; and detecting an amplified product of the parvovirus B19 nucleic acid by using a labeled detection probe that hybridizes specifically with the amplified product, thereby indicating presence of parvovirus B19 nucleic acid in the biological sample. In some embodiments, the amplifying step uses at least two oligomers selected from the following group of oligomer pairs: SEQ ID NO:4 including a promoter sequence joined to the 5' terminus, with SEQ ID NO:13, SEQ ID NO:6 including a promoter sequence joined to the 5' terminus, with SEQ ID NO:13, SEQ ID NO:24 including a promoter sequence joined to the 5' terminus, with SEQ ID NO:13, and SEQ ID NO:26 including a promoter sequence joined to the 5' terminus, with SEQ ID NO:13. Embodiments include an amplifying step that uses an amplification reaction that is substantially isothermal. In some embodiments, the detecting step uses a labeled detection probe selected from the group consisting of SEQ ID NO:17, SEQ ID NO:18, SEQ ID NO:27, SEQ ID NO:28, SEQ ID NO:30, SEQ ID NO:31, SEQ ID NO:32, SEQ ID NO:34, SEQ ID NO:36, and SEQ ID NO:37. In other embodiments, the labeled detection probe is selected from the group consisting of SEQ ID NO:17, SEQ ID NO:27, and SEQ ID NO:28. Some embodiments use a labeled detection probe with a backbone that includes at least one 2'-O-methoxy linkage. Embodiments of the detecting step may use a labeled detection probe that includes a label that is detected in a homogeneous reaction. In some embodiments, the labeled detection probe includes a chemiluminescent label attached to the oligomer via a linker compound. One embodiment of the method further includes the steps of contacting the biological sample with at least one capture oligomer comprising a target-specific sequence that hybridizes to a parvovirus B19 target sequence, thus forming a complex comprising the capture oligomer and parvovirus B19 nucleic acid; and separating the complex from the biological sample before the amplifying step. In some embodiments, the method uses a capture oligomer that comprises at least 25 contiguous bases of a target-specific sequence contained in SEQ ID NO:1, SEQ ID NO:2, SEQ ID NO:20, or SEQ ID NO:21, or RNA equivalents thereof. In some embodiments, the backbone of the capture oligomer includes at least one 2'-O-methoxy linkage.

It should be understood that both the foregoing general description and the following detailed description are exemplary only and are not restrictive of the invention. The detailed description and examples illustrate various embodiments and explain the principles of the invention.

DETAILED DESCRIPTION OF THE INVENTION

This application discloses oligonucleotide sequences used as primers for amplification and probes for detection of parvovirus B19 nucleic acid sequences present in a biological sample using an assay that includes in vitro nucleic acid amplification. A preferred embodiment of the method uses transcription-mediated nucleic acid amplification (as previously disclosed in detail in U.S. Pat. Nos. 5,399,491 and 5,554,516 to Kacian et al.). Preferred methods for detecting amplified nucleic acid include using sequence-specific probes that hybridize specifically to a portion of the amplified sequences. Preferably, the method uses any known homogeneous detection step to detect, in a mixture, a labeled probe that is bound to an amplified nucleic acid (e.g., as disclosed by Arnold et al., *Clin. Chem.* 35:1588–1594 (1989); U.S. Pat. No. 5,658,737 to Nelson et al., and U.S. Pat. Nos. 5,118,801 and 5,312,728 to Lizardi et al.). This application also discloses oligonucleotide sequences that are useful for capturing the parvovirus B19 target DNA by using nucleic acid hybridization techniques. One embodiment of the capturing step uses magnetic particles to separate the captured target (see U.S. Pat. No. 6,110,678 to Weisburg et al.).

By "biological sample" is meant any tissue or material derived from a living or dead human which may contain parvovirus nucleic acid, including, for example, sputum, peripheral blood, plasma, serum, biopsy tissue including lymph nodes, respiratory tissue or exudates, or other body fluids, tissues or materials. The sample may be treated to physically, chemically and/or mechanically disrupt tissue or cell structure, thus releasing intracellular components. Sample preparation may use a solution that contains buffers, salts, detergents and the like which are used to prepare the sample for analysis.

By "nucleic acid" is meant a multimeric compound comprising nucleosides or nucleoside analogs which have nitrogenous heterocyclic bases, or base analogs, linked together by nucleic acid backbone linkages (e.g., phosphodiester bonds) to form a polynucleotide. Conventional RNA and DNA are included in the term "nucleic acid" as are analogs thereof. The nucleic acid backbone may include a variety of linkages, for example, one or more of sugar-phosphodiester linkages, peptide-nucleic acid bonds (see PCT No. WO 95/32305 by Hydig-Hielsen et al.), phosphorothioate or methylphosphonate linkages or mixtures of such linkages in a single oligonucleotide. Sugar moieties in the nucleic acid may be either ribose or deoxyribose, or similar compounds with known substitutions, such as, for example, 2' methoxy substitutions and 2' halide substitutions (e.g., 2'-F). Conventional nitrogenous bases (A, G, C, T, U), known base analogs (e.g., inosine; see *The Biochemistry of the Nucleic Acids* 5–36, Adams et al., ed., 11$^{th}$ ed., 1992), derivatives of purine or pyrimidine bases (e.g., N$^4$-methyl deoxygaunosine, deaza- or aza-purines and deaza- or aza-pyrimidines, pyrimidines having a substituent at the 5 or 6 positions, purine bases having a substituent at the 2, 6 or 8 positions, 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines; PCT No. WO 93/13121 by Cook) and "abasic" residues (i.e., no nitrogenous base for one or more backbone positions) (U.S. Pat. No. 5,585,481 to Arnold et al.) are included in the term nucleic acid. That is, a nucleic acid may comprise only conventional sugars, bases and linkages found in RNA and DNA, or may include both conventional components and substitutions (e.g., conventional bases and analogs linked via a methoxy backbone, or conventional bases and one or more base analogs linked via an RNA or DNA backbone).

The backbone of an oligomer may affect stability of a hybridization complex (e.g., formed between of a capture oligomer to its target nucleic acid). Such embodiments include peptide linkages, 2'-O-methoxy linkages and sugar-phosphodiester type linkages. Peptide nucleic acids are advantageous for forming a hybridization complex with RNA. An oligomer having 2'-methoxy substituted RNA groups or a 2'-fluoro substituted RNA may have enhance hybridization complex stability relative to standard DNA or RNA and is preferred for forming a hybridization complex with a complementary 2'-OH RNA. A linkage joining two sugar groups may affect hybridization complex stability by affecting the overall charge or the charge density, or by affecting steric interactions (e.g., bulky linkages may reduce hybridization complex stability). Preferred linkages include those with neutral groups (e.g., methylphosphonates) or charged groups (e.g., phosphorothioates) to affect complex stability.

By "oligonucleotide" or "oligomer" is meant a nucleic acid having generally less than 1,000 residues, including polymers in a size range having a lower limit of about 5 nucleotide residues and an upper limit of about 500 nucleotide residues. Oligomers of some embodiments of the invention are in a size range having a lower limit of about 5 to about 15 residues and an upper limit of about 50 to 100 residues. Preferred embodiments of oligomers are in a size range having a lower limit of about 10 to about 25 residues and an upper limit of about 25 to about 60 residues. Oligomers may be purified from naturally occurring sources, but generally are synthesized in vitro by using any well known enzymatic or chemical method. Generally, when an oligomer of the present invention is synthesized in vitro with a 2'-O-methoxy backbone, a uracil (U) base is used in those positions that are occupied by a thymine (T) base in the same sequence in an oligomer synthesized with sugar-phosphodiester linkages, except for a 3' T which is a standard deoxynucleotide. That is, methoxy oligonucleotides have a methoxy group at the 2' position of the ribose moiety, and a U at the base position of a T residue in a standard DNA oligonucleotide, except when a T is present at the 3' end of the oligomer. When an oligomer is specified as containing an "OMeT" residue, the base position is occupied by a T residue and the backbone comprises 2'-O-methoxy linkages. Although an oligomer base sequence frequently is referred to as a DNA sequence (i.e., contains T residues), one skilled in the art will appreciate that the corresponding RNA sequence (i.e., the same base sequence but containing U in place of T), or the complementary DNA or RNA sequences are substantially equivalent embodiments of the specified DNA sequence. Indeed, as described above, an oligomer with a 2'-O-methoxy backbone may contain a mixture of U and T bases in the same oligomer.

By "amplification oligonucleotide" or "amplification oligomer" is meant an oligonucleotide that hybridizes to a target nucleic acid, or its complementary strand, and participates in nucleic acid amplification. Examples include primers and promoter-primers. Preferably, an amplification oligonucleotide contains at least 10 contiguous bases, and more preferably at least about 12 contiguous bases but less than about 65 bases, that hybridize specifically with a region of the target nucleic acid sequence (or a complementary strand thereof) under standard hybridization conditions. The contiguous bases that hybridize to the target sequence are at least about 80%, preferably at least about 90%, and more preferably about 100% complementary to the sequence to which the amplification oligonucleotide hybridizes. An amplification oligonucleotide is preferably about 20 to about 60 nt long (e.g., 21 to 56 nt) and optionally may include modified nucleotides.

Amplification oligomers may be referred to as "primers" or "promoter-primers." A "primer" refers to an oligonucleotide that hybridizes to a template nucleic acid and has a 3' end that can be extended in a known polymerization reaction. The 5' region of the primer may be non-complementary to the target nucleic acid, e.g., the 5' non-complementary region may include a promoter sequence and the oligomer is referred to as a "promoter-primer." Those skilled in the art will appreciate that any oligomer that can function as a primer (i.e., an amplification oligonucleotide that hybridizes specifically to a target sequence and has a 3' end that can be extended by a polymerase) can be modified to include a 5' promoter sequence, and thus function as a promoter-primer. Similarly, any promoter-primer can be modified by removal of, or synthesis without, a promoter sequence and function as a primer.

"Amplification" refers to any known procedure for obtaining multiple copies of a target nucleic acid sequence or its complement or fragments thereof, and preferred embodiments amplify the target specifically by using sequence-specific methods. Known amplification methods include, for example, transcription-mediated amplification, replicase-mediated amplification, polymerase chain reaction (PCR) amplification, ligase chain reaction (LCR) amplification and strand-displacement amplification (SDA). Replicase-mediated amplification uses self-replicating RNA molecules, and a replicase such as QB-replicase (e.g., see U.S. Pat. No. 4,786,600 to Kramer et al. and PCT No. WO 90/14439). PCR amplification is well known and uses DNA polymerase, sequence-specific primers and thermal cycling to synthesize multiple copies of the two complementary strands of DNA or cDNA (e.g., U.S. Pat. Nos. 4,683,195, 4,683,202, and 4,800,159 to Mullis et al., and *Methods in Enzymology*, 1987, Vol. 155: 335–350). LCR amplification uses at least four separate oligonucleotides to amplify a target and its complementary strand by using multiple cycles of hybridization, ligation, and denaturation (EP Patent No. 0 320 308). SDA amplifies by using a primer that contains a recognition site for a restriction endonuclease which nicks one strand of a hemimodified DNA duplex that includes the target sequence, followed by amplification in a series of primer extension and strand displacement steps (U.S. Pat. No. 5,422,252 to Walker et al.) As illustrated below, preferred embodiments use transcription-associated amplification. It will be apparent to one skilled in the art that method steps and amplification oligonucleotides of the present invention may be readily adapted to a variety of nucleic acid amplification procedures based on primer extension by a polymerase activity.

Amplification of a "fragment" or "portion" of the target sequence refers to production of an amplified nucleic acid containing less than the entire target region nucleic acid sequence or its complement. Such fragments may be produced by amplifying a portion of the target sequence, e.g., by using an amplification oligonucleotide which hybridizes to and initiates polymerization from an internal position in the target sequence.

By "transcription-mediated amplification" (TMA) or "transcription-associated amplification" is meant a nucleic acid amplification that uses an RNA polymerase to produce multiple RNA transcripts from a nucleic acid template. Transcription-associated amplification generally employs RNA polymerase and DNA polymerase activities, deoxyribonucleoside triphosphates, ribonucleoside triphosphates, and a promoter-primer, and optionally may include one or more other amplification oligonucleotides, including "helper" oligomers. Variations of transcription-associated amplification are well known in the art and described in detail elsewhere (see U.S. Pat. Nos. 5,399,491 and 5,554, 516 to Kacian et al., U.S. Pat. No. 5,437,990 to Burg et al., U.S. Pat. No. 5,130,238 to Malek et al., U.S. Pat. Nos. 4,868,105 and 5,124,246 to Urdea et al., PCT No. WO 93/22461 by Kacian et al., PCT Nos. WO 88/01302 and WO 88/10315 by Gingeras et al., PCT No. WO 94/03472 by McDonough et al., and PCT No. WO 95/03430 by Ryder et al.). The procedures of U.S. Pat. Nos. 5,399,491 and 5,554, 516 are preferred amplification embodiments.

By "probe" is meant a nucleic acid oligomer that hybridizes specifically to a target sequence in a nucleic acid, preferably in an amplified nucleic acid, under conditions that allow hybridization, thereby allowing detection of the target or amplified nucleic acid. Detection may either be direct (i.e., resulting from a probe hybridizing directly to the sequence) or indirect (i.e., resulting from a probe hybridizing to an intermediate molecular structure that links the probe to the target). The probe's "target" generally refers to a sequence within or a subset of an amplified nucleic acid sequence which hybridizes specifically to at least a portion of a probe oligomer by standard hydrogen bonding (i.e., base pairing). A probe may comprise target-specific sequences and other sequences that contribute to three-dimensional conformation of the probe (e.g., U.S. Pat. Nos. 5,118,801 and 5,312,728 to Lizardi et al., and U.S. Pat. No. 6,361,945 B1 to Becker et al.). Sequences are "sufficiently complementary" if they allow stable hybridization in appropriate hybridization conditions of a probe oligomer to a target sequence that is not completely complementary to the probe's target-specific sequence.

By "sufficiently complementary" is meant a contiguous nucleic acid base sequence that is capable of hybridizing to another base sequence by hydrogen bonding between a series of complementary bases. Complementary base sequences may be complementary at each position in the oligomer sequence by using standard base pairing (e.g., G:C, A:T or A:U) or may contain one or more residues that are not complementary (including abasic positions), but in which the entire complementary base sequence is capable of specifically hybridizing with another base sequence in appropriate hybridization conditions. Contiguous bases are preferably at least about 80%, more preferably at least about 90%, and most preferably 100% complementary to a sequence to which an oligomer is intended to hybridize. Those skilled in the art can readily choose appropriate hybridization conditions which can be predicted based on base sequence composition, or be determined by using routine testing (e.g., see Sambrook et al., *Molecular Cloning, A Laboratory Manual,* 2$^{nd}$ ed. (Cold Spring Harbor Laboratory Press, Cold Spring Harbor, N.Y., 1989) at §§ 1.90–1.91, 7.37–7.57, 9.47–9.51 and 11.47–11.57, particularly §§ 9.50–9.51, 11.12–11.13, 11.45–1147 and 11.55–11.57).

By "capture oligonucleotide" or "capture oligomer" or "capture probe" is meant a nucleic acid oligomer that hybridizes specifically to a target nucleic acid to be captured and provides a means for isolating and/or concentrating the target from other sample components. Embodiments of capture oligomers include two binding regions: a target-binding region and an immobilized probe-binding region, whereby the capture oligomer forms a hybridization complex in which the target-binding region of the capture oligomer binds to the target sequence and the immobilized probe-binding region binds to an oligomer immobilized on a solid support (see U.S. Pat. Nos. 6,110,678 and 6,280,952 to Weisburg et al.). Although the target-binding region and immobilized probe-binding region are usually on the same capture oligomer, the two functional regions may be present on two different oligomers joined together by one or more linkers. For example, an immobilized probe-binding region may be present on a first oligomer, a target-binding region may be present on a second oligomer, and the two oligomers are joined by hydrogen bonding with a third oligomer that is a linker that hybridizes specifically to sequences of the first and second oligomers. The target-binding region of a capture probe may also be referred to as a target-specific portion of the capture probe and the immobilized probe-binding region may be referred to as a tail portion. Embodiments of tail portions include homopolymers (e.g., poly-dT or poly-dA) or non-homopolymers (e.g., $T_{1-3}A_{30}$), preferably attached to the 3' end of the target-specific portion of the oligomer.

By "immobilized probe" or "immobilized oligomer" is meant a nucleic acid oligomer that joins, directly or indirectly, a capture oligomer to an immobilized support. An immobilized probe joined to a solid support facilitates separation of bound target sequence from unbound material in a sample. Any known solid support may be used, such as matrices and particles in solution, e.g., nitrocellulose, nylon, glass, polyacrylate, mixed polymers, polystyrene, silane polypropylene and metal particles, preferably, magnetically attractable particles. Preferred supports are monodisperse paramagnetic spheres (e.g., uniform size ±5%), to provide consistent results, to which an immobilized probe is joined directly (e.g., via a direct covalent linkage, chelation, or ionic interaction), or indirectly (e.g., via one or more linkers), where the linkage or interaction is stable during nucleic acid hybridization conditions.

By "separating" or "purifying" is meant that one or more components of the biological sample are removed from at least one other component of the sample. Sample components generally include an aqueous solution of nucleic acids, salts, proteins, carbohydrates, and lipids. A step of separating or purifying a nucleic acid removes at least about 70%, preferably at least about 90% and, more preferably, at least about 95% of the other components in the sample.

By "label" is meant a molecular moiety or compound that can be detected or can lead to a detectable signal. A label is joined, directly or indirectly, to a nucleic acid probe. Direct labeling uses bonds or interactions that link the label to the probe, including covalent bonds or non-covalent interactions, such as hydrogen bonds, hydrophobic and ionic interactions, or through formation of chelates or coordination complexes. Indirect labeling uses a bridging moiety or "linker" (e.g., oligonucleotide or antibody), to link the label and probe. Linkers can be used to amplify a detectable signal. Labels are any known detectable moiety, e.g., radionuclide, ligand (e.g., biotin, avidin), enzyme or enzyme substrate, reactive group, or chromophore, such as a dye or detectable particle (e.g., latex beads or metal particles), luminescent componds (e.g., bioluminescent, phosphorescent or chemiluminescent labels) and fluorescent compounds. Preferably, the label on a labeled probe is detectable in a homogeneous reaction (i.e., in a mixture, bound labeled probe exhibits a detectable change, such as stability or differential degradation, compared to unbound labeled probe). One embodiment of a label for use in a homogenous assay is a chemiluminescent compound (e.g., described in detail in U.S. Pat. No. 5,656,207 to Woodhead et al., U.S. Pat. No. 5,658,737 to Nelson et al., and U.S. Pat. No. 5,639,604 to Arnold, Jr., et al.). Preferred chemiluminescent labels are acridinium ester (AE) compounds, such as standard AE or derivatives thereof (e.g., naphthyl-AE, ortho-AE, 1- or 3-methyl-AE, 2,7-dimethyl-AE, 4,5-dimethyl-AE, ortho-dibromo-AE, ortho-dimethyl-AE, meta-dimethyl-AE, ortho-methoxy-AE, ortho-methoxy(cinnamyl)-AE, ortho-methyl-AE, ortho-fluoro-AE, 1- or 3-methyl-ortho-fluoro-AE, 1- or 3-methyl-meta-difluoro-AE, and 2-methyl-AE). Synthesis and methods of attaching labels to nucleic acids and detecting labels are well known in the art (e.g., Sambrook et al., *Molecular Cloning, A Laboratory Manual*, 2nd ed. (Cold Spring Harbor Laboratory Press, Cold Spring Habor, N.Y., 1989), Chapter 10; U.S. Pat. No. 4,581,333 to Kourilsky et al., U.S. Pat. No. 5,658,737 to Nelson et al., U.S. Pat. No. 5,656,207 to Woodhead et al., U.S. Pat. No. 5,547,842 to Hogan et al., U.S. Pat. No. 5,283,174 to Arnold, Jr. et al., and EP Patent Pub. No. 0747706 by Becker et al.). Another embodiment of a label for use in a homogenous assay is a fluorescent compound attached to a probe with a quencher compound in functional proximity to the fluorescent label when the probe is not hybridized to its target (e.g., U.S. Pat. Nos. 5,118,801 and 5,312,728 to Lizardi et al., and U.S. Pat. No. 6,361,945 B1 to Becker et al.).

A "homogeneous detectable label" refers to a label whose presence can be detected in a homogeneous fashion based upon whether the labeled probe is hybridized to a target sequence (i.e., can be detected without physically removing unhybridized label or labeled probe). Embodiments of homogeneous detectable labels and methods of detecting them have been described (U.S. Pat. No. 5,283,174 to Arnold et al., U.S. Pat. No. 5,656,207 to Woodhead et al., U.S. Pat. No. 5,658,737 to Nelson et al., U.S. Pat. Nos. 5,118,801 and 5,312,728 to Lizardi et al., and U.S. Pat. No. 6,361,945B1 to Becker et al.). al.).

By "consisting essentially of" is meant that additional component(s) and method step(s)] that do not materially change the basic and novel characteristics of the present invention may be included. Such characteristics include salts, buffering agents, nucleic acid oligomers and similar biochemical reagents that do not have a material effect on the characteristics of the claimed components or method steps described herein that detect parvovirus B19 nucleic acid sequences, including nucleic amplification products derived from parvovirus B19 DNA, with a sensitivity of about 100 to 500 copies of parvovirus B19 DNA in the starting material. Similarly, additional method steps that do not have a material effect on the basic nature of the assay may be included.

Assays of the present invention detect human parvovirus present in a biological sample (e.g., blood, serum, plasma, sputum, bronchial lavage). In one embodiment, the assay detected parvovirus B19 DNA in plasma samples, either pooled or from individual donors. To prepare plasma specimens, whole blood samples were centrifuged using standard methods, and the plasma was stored at 4° C. or −20° C. before testing. To lyse viral particles in the specimen, a lysing reagent containing a detergent was mixed with the specimen to release the parvovirus B19 DNA from viral particles. Specimen processing may combine viral lysis with purification of the viral target DNA by including a capture oligomer and immobilized oligomer in the lysing reagent. Then the method includes a target capture step in which the parvovirus B19 DNA is hybridized specifically to the capture oligomer, which is then hybridized to the immobilized oligomer, and the bound complex (i.e., immobilized oligomer, capture oligomer, and viral target DNA) is substantially separated from other sample components. Residual sample components are washed away by washing the solid support with the bound parvovirus-containing complex. Thus, the viral target DNA is separated form other sample components and concentrated in the bound complexes, without releasing the bound parvovirus B19 nucleic acid from the solid support.

Typical sample processing involved the following steps (described in detail in U.S. Pat. No. 6,110,678). Viral particles in body fluid (e.g., 0.5 ml of plasma) were lysed upon contact at 60° C. with target capture reagent (790 mM HEPES, 680 mM LiOH, 10% lithium lauryl sulfate (LLS), 230 mM succinate, at least one capture probe at 7 pm/ml, and 100 μg/ml of poly-$dT_{14}$ bound to magnetic particles (SERADYN™, Indianapolis, Ind.)). Capture oligomers were composed of 5' target-specific sequence (e.g., SEQ ID NOS. 1, 2, 20 and 21) that is complementary to and hybridizes specifically to a target sequence that is a portion of the parvovirus B19 genome sequence, and a 3' tail sequence (e.g., oligo-dA) that hybridizes to the complementary oligmer (e.g., oligo-dT) attached to the solid support. Other preferred embodiments of capture probes are oligomers that contain a target-complementary sequence of 27 to 33 nucleotides that includes SEQ ID NO:41, and oligomers that bind specifically to the target sequences shown in SEQ ID NO:22 and SEQ ID NO:29. Target capture hybridization occurs in this reaction mixture by incubating the mixture at a first temperature (60° C.), allowing the capture oligomer to bind specifically to its complementary target sequence in parvovirus B19 DNA. Then, the mixture was cooled to 40° C. or lower (e.g., room temperature) to allow the 3' tail of the capture oligomer to hybridize to its complementary oligomer on the particle. Following the second hybridization, the mixture is treated to separate the solid support with its bound complex of nucleic acids from the other sample components, e.g., by using gravitational, centrifugal, or magnetic separation. Generally, separation employed a rack that contains a magnet to pull the magnetic particles with bound nucleic acid complexes to the side of the tube. Then the supernatant was removed and the bound complexes on the particles were washed with 1 ml of a washing buffer (10 mM HEPES, 6.5 mM NaOH, 1 mM EDTA, 0.3% (v/v) absolute ethanol, 0.02% (w/v) methyl paraben, 0.01% (w/v) propyl paraben, 150 mM NaCl, 0.1% sodium dodecyl sulfate (SDS), pH 7.5) by suspending the magnetic particles in washing buffer, separating particles to the tube side, and removing the supernatant.

Following sample preparation, amplification of the parvovirus B19 DNA target was achieved by using a pair of amplification oligomers that define the 5' and 3' ends of the region amplified by in vitro enzyme-mediated nucleic acid synthesis. One embodiment uses a transcription-mediated amplification (TMA) method, substantially as described in U.S. Pat. Nos. 5,399,491 and 5,554,516, which is a substantially isothermal system that produces a large number of amplification products (RNA transcripts) that can be detected. Embodiments of the method used mixtures of amplification oligomers in which at least one promoter primer is selected from the group consisting of SEQ ID NO:3, SEQ ID NO:5, SEQ ID NO:7, SEQ ID NO:9, SEQ ID NO:11, SEQ ID NO:23, and SEQ ID NO:25, which is combined with at least one primer selected from the group consisting of SEQ ID NO:13, SEQ ID NO:14, SEQ ID NO:15, and SEQ ID NO:16. Other embodiments used mixtures of amplification oligomers in which at least one promoter primer is selected from the group consisting of SEQ ID NO:3, SEQ ID NO:5, and SEQ ID NO:9, which is combined with at least one primer selected from the group consisting of SEQ ID NO:13 and SEQ ID NO:16. Some embodiments used mixtures of amplification oligomers in which at least one promoter primer is selected from the group consisting of SEQ ID NO:3, SEQ ID NO:23, and SEQ ID NO:25, which is combined with a primer consisting of SEQ ID NO:13. One skilled in the art will appreciate that oligomers consisting of the target-specific portions of promoter primers can hybridize to the target sequence and provide a 3' end to function as a primer for enzyme-mediated nucleic acid amplification, independent of its promoter sequence (SEQ ID NO:19). Such oligomers include the sequences of SEQ ID NO:4, SEQ ID NO:6, SEQ ID NO:8, SEQ ID NO:10, SEQ ID NO:12, SEQ ID NO:24, and SEQ ID NO:26.

Amplifying the target nucleic acid by transcription-mediated amplification produces many strands of nucleic acid from a single copy of target nucleic acid, thus permitting detection of the target by detecting probes that hybridize to the amplified sequences. Generally, the reaction mixture includes the target nucleic acid and two primers, including at least one promoter primer, reverse transcriptase and RNA polymerase activities, nucleic acid synthesis substrates (deoxyribonucleoside triphosphates and ribonucleoside triphosphates) and appropriate salts and buffers in solution to produce multiple RNA transcripts from a nucleic acid template. Briefly, a first promoter-primer hybridizes specifically to a portion of the target sequence and reverse transcriptase that includes RNase H activity creates a first strand cDNA by 3' extension of the promoter-primer. The cDNA is hybridized with a second primer downstream from the first promoter primer and a new DNA strand is synthesized from the 3' end of the second primer using the reverse transcriptase to create a dsDNA having a functional promoter sequence at one end. RNA polymerase binds to the dsDNA at the promoter sequence and transcribes multiple transcripts or "amplicons." These amplicons are further used in the amplification process, serving as a template for a new round of replication, to ultimately generate large amounts of single-stranded amplified nucleic acid from the initial target sequence (e.g., 100 to 3,000 copies of RNA synthesized from a single template). The process uses substantially constant reaction conditions (i.e., substantially isothermal). A typical 100 µl amplification reaction uses 75 µl of an amplification reagent mixture (11.6 mM Tris Base, 15.0 mM Tris-HCl, 22.7 mM $MgCl_2$, 23.3 mM KCl, 3.33% glycerol, 0.05 mM Zn-acetate (dihydrate), 0.665 mM each of dATP, dCTP, dGTP, and dTTP, 5.32 mM each of ATP, CTP, GTP, and UTP, pH 7) and 25 µl of an enzyme reagent mixture (700 U of T7 RNA polymerase, 1400 U of reverse transcriptase from Moloney Murine Leukemia Virus (MMLV-RT), 16 mM HEPES (free acid, dihydrate), 70 mM N-acety-L-cysteine, 3 mM EDTA, 0.05% (w/v) Na-azide, 20 mM Tris base, 50 mM KCl, 20% (v/v) anhydrous glycerol, 10% (v/v) TRITON®) X-102, and 150 mM trehalose (dihydrate), pH 7), preferably mixed with the captured target nucleic acid retained on the solid particles. For the enzymatic activities, 1 U of T7 RNA polymerase incorporates 1 nmol of ATP into RNA in 1 hr at 37° C. using a DNA template containing a T7 promoter, and 1 U of MMLV-RT incorporates 1 nmol of dTTP into DNA in 10 min at 37° using 200–400 µmol oligo dT-primed poly(A) as a template.

Following amplification, the amplified sequences generated from the parvovirus B19 target DNA are detected, preferably by hybridization with at least one labeled nucleic acid probe that hybridizes specifically to a portion of the amplified sequence. Probe embodiments include those having a $T_m$ in the range of about 80° C. to 85° C. Some probe embodiments include oligomers having sequences of SEQ ID NO:17, SEQ ID NO:18, SEQ ID NO:27, SEQ ID NO:28, SEQ ID NO:30, SEQ ID NO:31, SEQ ID NO:32, SEQ ID NO:34, SEQ ID NO:36, and SEQ ID NO:37. Other embodiments are oligomers of 20 to 22 nucleotides that include sequences contained in SEQ ID NO:38, SEQ ID NO:39, or SEQ ID NO:40. Other probe embodiments include oligomers of at least 21 contiguous nucleotides contained in SEQ ID NO:33, and oligomers of 20 to 25 contiguous nucleotides contained in SEQ ID NO:35. Detection of the labeled probe is preferably accomplished by detecting a label that can be detected in a homogeneous reaction. Therefore, some embodiments include probes labeled with an acridinium ester (AE) compound using well-known methods that allow homogeneous detection (e.g., labels and detection methods are described in detail in U.S. Pat. No. 5,283,174 to Arnold, Jr., et al., U.S. Pat. No. 5,656,207 to Woodhead et al., and U.S. Pat. No. 5,658,737 to Nelson et al.). A chemiluminescent AE compound is attached to the probe sequence via a linker compound (substantially as described in U.S. Pat. Nos. 5,585,481 and 5,639,604 to Arnold, Jr., et al., e.g., see column 10, line 6 to column 11, line 3, and Example 8). In some embodiments, AE compound labels were linked to SEQ ID NO:17 between positions 7 and 8 or positions 11 and 12, and to SEQ ID NO:18 between positions 11 and 12. Additional embodiments of labeled probes are described in Example 9. In one embodiment, the labeled probe oligomer has at least one 2'-O-methoxy linkage in the nucleic acid backbone (e.g., SEQ ID NO:18 synthesized with a 2'-O-methoxy backbone). In a typical detection step, the probe reagent included 100 mM succinate, 2% (w/v) LLS, 230 mM LiOH (monohydrate), 15 mM 2,2'-dithiodipyridine (ALDRITHIOL-2),1.2 M LiCl, 20 mM EDTA, 20 mM EGTA, 3% (v/v) absolute ethanol, brought to about pH 4.7 with LiOH, and the selection reagent used for hydrolyzing the label on unbound probe included 600 mM boric acid, 182 mM NaOH, 1% (v/v) TRITON® X-100. The signal was detected as relative light units (RLU) using a luminometer (e.g., LEADER™ 450HC+, Gen-Probe Incorporated, San Diego, Calif.).

To select DNA sequences appropriate for use as capture oligomers, amplification oligomers and detection probes, known parvovirus B19 DNA sequences, including partial or complementary sequences, available from publicly accessible databases (e.g., GenBank) were aligned by matching regions of the same or similar sequences and compared using well known molecular biology techniques. Although sequence comparisons may be facilitated by use of algorithms, those skilled in the art can readily perform such comparisons manually and visually. Generally, portions of sequences that contain relatively few variants between the compared sequences were chosen as a basis for designing synthetic oligomers for use in the present invention. Other considerations in designing oligomers included the relative GC content (which affects $T_m$) and the relative absence of predicted secondary structure (which potentially form intramolecular hybrids) within a sequence, as determined by using well known methods.

In one embodiment, the assay is carried out in a single tube using a 0.5 to 1 ml sample of body fluid (e.g., plasma) to detect target parvovirus B19 DNA at a sensitivity of about 100 to 500 copies/ml of target DNA per reaction. In other embodiments, the assay detected higher numbers of target parvovirus B19 DNA in the sample, which may be a pooled sample of individual samples.

Unless defined otherwise, all scientific and technical terms used herein have the same meaning as commonly understood by those skilled in the relevant art. General definitions of many of the terms used herein are provided in *Dictionary of Microbiology and Molecular Biology*, 2nd ed. (Singleton et al., 1994, John Wiley & Sons, New York, N.Y.), *The Harper Collins Dictionary of Biology* (Hale & Marham, 1991, Harper Perennial, New York, N.Y.), and *Taber's Cyclopedic Medical Dictionary*, 17th ed. (F.A. Davis Co., Philadelphia, Pa., 1993). Unless mentioned otherwise, the techniques employed or contemplated herein are standard methodologies well known to one of ordinary skill in the art. The following examples illustrate some of the preferred embodiments of the invention and are provided for illustration only.

EXAMPLE 1

Target Capture of Parvovirus B19 DNA

Capture probes were synthesized having sequences of SEQ ID NO: 1 and SEQ ID NO:2, both having 3' $dA_{30}$ tails, using standard in vitro DNA synthesis reactions. Using the target capture methods described above, the capture oligomers were mixed with human plasma samples obtained from uninfected donors, each sample spiked with a known number of copies of live parvovirus B19 (2,000, 1,000, 500 or 0 in the negative control). The virions were lysed by mixing the plasma sample (generally 0.5 ml) with an equal volume of target capture reagent containing each of the capture probes separately (3.5 pm per reaction). Following capture by hybridization at about 60° C. for about 20 min and then at 18–25° C. for about 10–20 min, the magnetic particles with attached hybridization complexes were washed twice as described above. The parvovirus target sequence in the complexes retained on the particles was amplified in a TMA reaction performed substantially as described in Example 2, and the amplified target sequences were detected by hybridization with a AE-labeled probe (SEQ ID NO:17). The results (RLU detected from bound detection probe) are shown in Table 1. These results (RLU of about $1.5 \times 10^6$) show that both capture probes specifically bind to and effectively capture parvovirus B19 DNA from a sample compared to the negative control (RLU about $2 \times 10^4$).

TABLE 1

Detection of labeled probe (RLU) bound to parvovirus B19 DNA following target capture.

| B19 copies per reaction | $A_{30}$ Capture Probe SEQ NO:1 | $A_{30}$ Capture Probe SEQ NO:2 |
|---|---|---|
| 2,000 | $1.56 \times 10^6$ | $1.61 \times 10^6$ |
| 1,000 | $1.42 \times 10^6$ | $1.53 \times 10^6$ |
| 500 | $1.58 \times 10^6$ | $1.59 \times 10^6$ |
| 0 | $1.98 \times 10^4$ | $2.44 \times 10^4$ |

EXAMPLE 2

Amplification of Parvovirus B19 DNA and Detection of Amplicons

A known amount of parvovirus B19 target nucleic acid (denatured ssDNA at 1000, 500, 250, 100, 50 and 0 copies per reaction tube) was amplified in a TMA reaction using reagents (75 μl per reaction) as described above containing a promoter primer of SEQ ID NO:3 and a primer of SEQ ID NO:13 (7.5 pmol each), and covered with 200 μl of inert silicone oil to prevent evaporation. The mixture was incubated 10 min at 60° C., then 10 min at 42° C. and then 25 μl of enzyme reagent was added and the tubes were mixed by hand and then incubated 60 min at 42° C. Following amplification the samples were incubated at 60° C. and 100 μl of probe reagent was added containing probe of SEQ ID NO:17. The mixture was incubated 20 min at 60° C. and then 300 μl of selection reagent was added, mixed, and incubated 10 min at 60° C. and 10 min at room temperature before detecting the signal (RLU) as described above.

Following such amplification and detection steps, the average signal detected from five replicate samples for each condition were: 1,000 copies produced $6.78 \times 10^6$ RLU, 500 copies produced $5.56 \times 10^6$ RLU, 250 copies produced $4.42 \times 10^6$ RLU, 100 copies produced $1.06 \times 10^6$ RLU, and 50 copies produced $2.03 \times 10^4$ RLU, all compared to a negative control (0 copies) that produced $1.64 \times 10^4$ RLU. These results show that the sensitivity of the amplification and detection assay is at least 100 copies of target.

EXAMPLE 3

Detection of Parvovirus B19 in an Amplification Assay that Uses Target Capture

In this example, the target capture assay performed substantially as described in Example 1 was combined with amplification and detection steps performed substantially as described in Example 2. The copies of virion were known (500, 250, 100 and 0 for the negative control) for each sample tested. The capture probes were as in Example 1, and the combinations of amplification oligomers were SEQ ID NO:3 with SEQ ID NO:13, and SEQ ID NO:5 with SEQ ID NO:13. The detection probe was SEQ ID NO:17. The results shown in Table 2 are for an average of 5 samples for each of the conditions tested. These results show that the sensitivity of the assay is about 250 copies of target parvovirus DNA in the sample or better (i.e., capable of detecting 100 copies per sample). The primer set of SEQ ID NO:3 plus SEQ ID NO:13 had sensitivity of better than 250 copies of virus in capture from plasma, as well has stable, reproducible signal with 100 copies sensitivity in an amplification and detection assay as described in Example 2.

TABLE 2

Detected signal (RLU) for target capture plus amplification assays.

| Oligomers | | Copies of Parvovirus B19 | | | |
|---|---|---|---|---|---|
| Capture | Amplification | 500 | 250 | 100 | 0 |
| SEQ ID NO:1 | SEQ ID NO:3 SEQ ID NO:13 | $1.30 \times 10^6$ | $1.30 \times 10^6$ | $9.86 \times 10^5$ | $3.30 \times 10^4$ |
|  | SEQ ID NO:5 SEQ ID NO:13 | $2.37 \times 10^6$ | $2.91 \times 10^5$ | $2.52 \times 10^5$ | $4.66 \times 10^4$ |
| SEQ ID NO:2 | SEQ ID NO:3 SEQ ID NO:13 | $9.65 \times 10^5$ | $8.88 \times 10^5$ | $7.85 \times 10^5$ | $1.15 \times 10^5$ |
|  | SEQ ID NO:5 SEQ ID NO:13 | $2.06 \times 10^5$ | $1.03 \times 10^5$ | $4.14 \times 10^4$ | $3.51 \times 10^3$ |

EXAMPLE 4

Clinical Specimen Testing

To determine assay specificity and prevalence of parvovirus B19 DNA in a normal blood donor population, the TMA-based assay was performed substantially as described in Example 3 (using amplification oligomers of SEQ ID Nos. 3 and 13) on clinical and commercially available plasma samples. The assay was performed on 468 random blood donor specimens that were negative for the presence of HIV and HCV (obtained from the Community Blood Center of Greater Kansas City, Kansas City, Mo.). Three specimens of 468 (0.6%) were positive for parvovirus B19 (i.e., provided a signal equivalent to that detected for at least 100 copies of target when compared to positive controls). All three positive samples provided positive results when they were retested using the same TMA-based assay and when tested using a PCR-based assay that amplifies a different target sequence of parvovirus B19.

The sensitivity of this TMA-based assay was estimated based on a standardized parvovirus B19 DNA specimen (obtained from the American Red Cross and quantified by the National Genetics Institute). Detection of positive samples containing 500 copies/ml and 200 copies/ml of the parvovirus B19 standard in the assay was 100% (10 of 10 tests) and 80% (8 of 10 tests), respectively. Another standard (obtained from the National Institute for Biological Standards and Controls, or NIBSC) that contains 1,000 genome equivalents/ml also tested positive in this assay. These results show that the assay has the sensitivity and specificity required for detecting human parvovirus B19 in a blood screening environment.

Several specimens that were antibody-positive for parvovirus B19 were also tested using this TMA-based assay. Four plasma samples positive for anti-parvovirus IgM (LM 00PP751, 05256–520, 05254–520, and 05259–520, from SeraCare Life Sciences, Inc., Oceanside, Calif.) all gave positive results for parvovirus B19 DNA when tested using the TMA-based assay, compared to the NIBSC standard as a positive control. Six specimens (obtained from Chiron Corp., Emeryville, Calif.) positive for anti-parvovirus antibodies and parvovirus B19 DNA (based on a PCR-based test) were diluted 1 to 10 into negative human plasma. The diluted samples were assayed using the TMA-based assay, and all six specimens tested positive for parvovirus B19, showing the high level of sensitivity of the assay. Six plasma specimens (from BioClinical Partners, Inc., Franklin, Mass., USA) positive for anti-parvovirus B19 IgM were also tested using the TMA-based assay. All six plasmas tested negative for parvovirus B19 nucleic acid, showing that the virus had cleared from the donors even though their plasma retained antibodies to parvovirus B19.

EXAMPLE 5

Sample Preparation Using Various Target Capture Oligomers

This example shows that various oligomers can be used alone or in combination in an initial step of the assay, i.e., capture of parvovirus B19 DNA from a sample by using hybridization to a capture oligomer. In these experiments, oligomers of SEQ ID NO:1, SEQ ID NO:20 and SEQ ID NO:21 were synthesized with a 3' poly(A) tail portion and used to capture parvovirus B19 DNA from a sample using procedures substantially as described previously (U.S. Pat. No. 6,110,678). Briefly, a plasma sample containing parvovirus B19 was mixed with a lysing and capture reagent containing one or more of the capture oligomers and the mixture was incubated (60° C., 20 min) to allow the capture oligomers to hybridize to the parvovirus target DNA. The mixture also contained homopolymeric oligomers complementary to the 3'-tail portion of the capture oligomer and attached to magnetic particles. These homopolymeric complementary sequences hybridized in a second hybridization reaction (25° C., 14–20 min) and the hybridization complexes attached to the magnetic particles were separated from the rest of the sample and washed (e.g., twice with 1 ml of a buffer than maintains the hybridization complexes on the particles) before proceeding to amplification. In these experiments, 3.5 pmol per reaction of each of the capture oligomers tested as follows: reactions included each of SEQ ID Nos 1, 20 and 21 individually, and in the various possible combinations (SEQ ID Nos 1 and 20, SEQ ID Nos 1 and 21, SEQ ID Nos 20 and 21, and SEQ ID Nos 1, 20 and 21). After the samples were treated with the capture reagent, the magnetic particles with the attached hybridization complexes were incubated in an amplification mixture containing 15 pmol per reaction of each of a promoter primer of SEQ ID NO:23 and a primer of SEQ ID NO:13, and the appropriate salts, nucleotides and enzymes for a one-hour TMA reaction (substantially as described in detail previously in U.S. Pat. Nos. 5,399,491 and 5,554,516). The detection probe of SEQ ID NO:17 labeled with 2-methyl-AE between nt 7 and nt 8 was added (0.1 pmol per reaction) and incubated (60° C., 20 min) with the amplification products to allow hybridization, and the chemiluminescent signal was detected (RLU) as described in detail previously (U.S. Pat. Nos. 5,283,174, 5,656,207, and 5,658,737).

In a first set of experiments, the tested human plasma samples contained no parvovirus B19 (negative samples) or 1,000 copies per reaction of parvovirus B19 (positive samples), which were prepared by dilution from a stock sample of infected plasma (from the American Red Cross) which had been titrated by comparison with a standardized sample (from NIBSC). Ten replicate samples were tested for each of the conditions. The detected results (RLU mean±standard deviation) are shown in the table that follows.

TABLE 3

Results of Assays Performed Using Different Capture Oligomers.

| Capture Oligomers | Negative Samples | Positive Samples |
|---|---|---|
| SEQ ID NO:1 | 2,461 ± 1,252 | 4,067,173 ± 163,492 |
| SEQ ID NO:20 | 2,137 ± 360 | 3,893,205 ± 477,513 |
| SEQ ID NO:21 | 4,774 ± 6,970 | 3,954,41 6 ± 468,324 |
| SEQ ID NO:1 + SEQ ID NO:20 | 5,285 ± 4,911 | 4,078,141 ± 269,686 |
| SEQ ID NO:1 + SEQ ID NO:21 | 2,560 ± 1,002 | 4,093,581 ± 271,294 |
| SEQ ID NO:20 + SEQ ID NO:21 | 2,164 ± 301 | 4,000,996 ± 361,454 |
| SEQ ID NO:1 + SEQ ID NO:20 + SEQ ID NO:21 | 4,291 ± 4,919 | 3,994,533 ± 116,348 |

In a second set of experiments, the plasma samples contained no parvovirus B19 (negative samples) or varying amounts of parvovirus B19 (1,000, 500, 250,100 and 50 copies per reaction), prepared by dilution from the stock sample described above. For each of the conditions, five replicate samples were tested for those containing 1,000 and 0 copies of parvovirus B19, and ten replicate samples were tested for all the others. The detected results (RLU mean±standard deviation) are shown below. For all of the negative controls (0 copies per reaction), the detected background was in the range of 2,277±215 to 4,724±3,889 RLU.

90% of samples that contained 100 copies/ml, and for 50 to 70% of samples that contained 50 copies/ml.

EXAMPLE 6

Amplification of Parvovirus B19 Sequences Using Different Amplification Oligomers This example shows that different combinations of amplification oligomers serving as primers can amplify efficiently the target sequences in parvovirus B19 DNA. The target sequences were amplified by using a combination of primers that had the parvovirus-specific portions of SEQ ID NO:24 (AGTACCGGGTAGTTGTACGCTAACT) or SEQ ID NO:26 (CTAGGTTCTGCATGACTGCTACTGGA) and SEQ ID NO:13 (CCCCTAGAAAACCCATCCTCT).

Samples were prepared by mixing a human plasma that does not contain parvovirus (negative control) with aliquots of parvovirus B19 to produce samples containing 10,000, 5,000, 1,000, 500, 250, 100, 50, and 25 copies of parvovirus B19 per ml. As a positive control, standard samples containing 1,000 copies of parvovirus B19 per ml were also assayed. The samples were mixed with an oligomer (SEQ ID NO:1) which was allowed to hybridize to the parvovirus B19 DNA, and then the hybridization complex containing the parvovirus B19 DNA was separated from the sample by hybridizing it to an oligomer attached to a magnetic bead, substantially as described previously (U.S. Pat. No. 6,110, 678).

The amplification assays were performed using the TMA system substantially as described above using 15 pmol each of the promoter primer of SEQ ID NO:23 and SEQ ID NO:13, or the promoter primer of SEQ ID NO:25 and SEQ ID NO:13. Following the one-hour amplification reaction, the mixtures were hybridized with a detection probe of SEQ ID NO:17 labeled with a chemiluminescent compound between nt 7 and 8 (using $5.5 \times 10^9$ RLU per reaction), and the relative light unit (RLU) signals were detected as

TABLE 4

Sensitivity of Assays Performed Using Different Capture Oligomers

| Capture Oligomers | Copies of Parvovirus B19 Per Reaction | | | | |
|---|---|---|---|---|---|
| SEQ ID NOs | 1,000 | 500 | 250 | 100 | 50 |
| 1 | $4.04 \times 10^6$ ± $4.18 \times 10^5$ | $3.80 \times 10^6$ ± $5.01 \times 10^5$ | $3.55 \times 10^6$ ± $8.04 \times 10^5$ | $1.89 \times 10^6$ ± $1.55 \times 10^6$ | $8.04 \times 10^5$ ± $1.34 \times 10^6$ |
| 20 | $4.00 \times 10^6$ ± $3.60 \times 10^5$ | $3.89 \times 10^6$ ± $5.63 \times 10^5$ | $2.78 \times 10^6$ ± $1.22 \times 10^5$ | $2.06 \times 10^6$ ± $1.59 \times 10^6$ | $1.85 \times 10^6$ ± $1.73 \times 10^5$ |
| 21 | $4.27 \times 10^6$ ± $5.85 \times 10^4$ | $4.00 \times 10^6$ ± $3.22 \times 10^5$ | $3.25 \times 10^6$ ± $1.24 \times 10^6$ | $1.26 \times 10^6$ ± $1.05 \times 10^6$ | $7.13 \times 10^5$ ± $1.28 \times 10^6$ |
| 1 and 20 | $4.14 \times 10^6$ ± $1.71 \times 10^6$ | $3.51 \times 10^6$ ± $1.34 \times 10^5$ | $3.57 \times 10^6$ ± $9.30 \times 10^5$ | $2.10 \times 10^6$ ± $1.66 \times 10^6$ | $1.13 \times 10^6$ ± $1.52 \times 10^6$ |
| 1 and 21 | $4.28 \times 10^6$ ± $8.45 \times 10^4$ | $3.78 \times 10^6$ ± $1.16 \times 10^6$ | $3.23 \times 10^6$ ± $1.08 \times 10^6$ | $1.60 \times 10^6$ ± $1.33 \times 10^6$ | $1.44 \times 10^6$ ± $1.60 \times 10^6$ |
| 20 and 21 | $4.15 \times 10^6$ ± $2.10 \times 10^5$ | $4.26 \times 10^6$ ± $1.49 \times 10^5$ | $2.68 \times 10^6$ ± $1.76 \times 10^6$ | $1.55 \times 10^6$ ± $1.69 \times 10^6$ | $1.06 \times 10^6$ ± $1.28 \times 10^6$ |
| 1, 20 and 21 | $4.24 \times 10^6$ ± $1.30 \times 10^5$ | $4.35 \times 10^6$ ± $1.09 \times 10^5$ | $2.56 \times 10^6$ ± $1.59 \times 10^6$ | 2,529,303 ± 1,652,537 | $9.62 \times 10^5$ ± $1.46 \times 10^6$ |

The results of these experiments show that when the assay was performed with any of the three capture oligomers, alone or in a mixture, each format detected the presence of parvovirus B19. The assays resulted in positive signals for all samples that contained 250 to 1,000 copies/ml, for 80 to described above. For the positive and negative controls, 5 replicate samples were tested. For the experimental samples, 10 replicates were tested for each condition. The results of these assays (RLU mean±standard deviation) are shown in the table that follows.

TABLE 5

Assay Results Obtained Using Different Amplification Oligomers

| Parvovirus B19 copies/ml | SEQ ID NO:13 and SEQ ID NO:23 Primers | SEQ ID NO:13 and SEQ ID NO:25 Primers |
|---|---|---|
| 1,000 (positive control) | $3.87 \times 10^6 \pm 1.89 \times 10^5$ | $2.53 \times 10^6 \pm 7.94 \times 10^5$ |
| 10,000 | $4.20 \times 10^6 \pm 8.27 \times 10^4$ | $4.03 \times 10^6 \pm 7.29 \times 10^5$ |
| 5,000 | $4.07 \times 10^6 \pm 2.73 \times 10^5$ | $3.97 \times 10^6 \pm 1.15 \times 10^5$ |
| 1,000 | $3.80 \times 10^6 \pm 7.38 \times 10^5$ | $2.77 \times 10^6 \pm 6.63 \times 10^5$ |
| 500 | $3.17 \times 10^6 \pm 1.09 \times 10^6$ | $1.82 \times 10^6 \pm 1.13 \times 10^6$ |
| 250 | $2.90 \times 10^6 \pm 7.57 \times 10^5$ | $1.07 \times 10^6 \pm 5.83 \times 10^5$ |
| 100 | $1.73 \times 10^6 \pm 1.54 \times 10^6$ | $3.79 \times 10^5 \pm 4.73 \times 10^5$ |
| 50 | $1.74 \times 10^6 \pm 1.74 \times 10^4$ | $2.34 \times 10^5 \pm 5.96 \times 10^5$ |
| 25 | $2.20 \times 10^5 \pm 5.66 \times 10^5$ | $2.52 \times 10^5 \pm 7.83 \times 10^5$ |
| 0 (negative control) | $2.73 \times 10^3 \pm 5.12 \times 10^2$ | $3.57 \times 10^3 \pm 2.37 \times 10^3$ |

The results show that both combinations of oligomers used as primers performed substantially equally in the assay to amplify parvovirus B19 sequences. In both assay formats, positive signals were detected for all of the samples containing 250 or more copies of parvovirus B19, and positive signals were detected for 70 to 80% of the samples containing 100 copies.

In similar experiments, the assay was performed using other combinations of primers: a promoter primer of SEQ ID NO:3 and SEQ ID NO:13, or a promoter primer of SEQ ID NO:23 and SEQ ID NO:13. The parvovirus B19-specific portions of these promoter primers are, respectively, SEQ ID NO:4 (CTAGGTTCTGCATGACTGCTACTGGA) and SEQ ID NO:24 (see above). The tested samples either contained no parvovirus B19 (negative controls) or 1,000 copies of parvovirus B19 per reaction. Ten replicate samples were tested for each condition. For the combination of primers of SEQ ID NO:3 and SEQ ID NO:13, the assay produced a mean RLU signal of 2,678,709±507,209 for positive samples and 1,841±128 for the negative controls. For the combination of primers of SEQ ID NO:23 and SEQ ID NO:13, the assay produced a mean RLU signal of 4,074,989±123,420 for positive samples and 3,462±2,936 for the negative controls. Thus, an additional combination of amplification oligomers can be used to perform the assay to detect the presence of parvovirus B19 DNA in a sample.

EXAMPLE 7

Parvovirus B19 Detection Assays Performed with Different Detection Probes

In this example, parvovirus B19 was assayed by using substantially the method described in Example 5. Briefly, samples were prepared using human plasma that contains no parvovirus (negative control), by adding known amounts of parvovirus B19 (to achieve final concentrations of 10,000, 5,000, 1,000, 500, 250, 100, 50, and 25 copies per ml). In addition to these, previously tested known samples containing 1,000 copies of parvovirus B19 per ml were included in the tests as positive controls. Samples were assayed by, first, capturing the parvovirus B19 DNA from a 1 ml sample by hybridization to a complementary oligomer (SEQ ID NO:1) which was then hybridized via its 3' poly(A) tail to a complementary poly(T)-oligomer attached to magnetic beads using procedures substantially as described previously (U.S. Pat. No. 6,110,678). Then, a target portion of the parvovirus B19 genomic sequence was amplified in a one-hour TMA reaction that included a promoter primer of SEQ ID NO:23 (comprising the target-specific sequence of SEQ ID NO:24 and a T7 RNA polymerase promoter sequence of SEQ ID NO:19) and a primer of SEQ ID NO:13. The amplification products were detected by using detection probes labeled with 2-methyl-AE in a reaction to detect relative light units (RLU) as described in detail previously (U.S. Pat. Nos. 5,585,481 and 5,639,604). The detection probes were synthesized by using standard chemical methods to produce oligomers with a 2'-O-methoxy backbone and having the nucleotide sequences of SEQ ID NO:17(label between nt 7 and 8), SEQ ID NO:27 (label between nt 5 and 6), and SEQ ID NO:28 (label between nt 9 and 10). Two separate sets of assays were performed, one in which the detection results were obtained by using SEQ ID Nos. 17 and 27, and another in which detection results were obtained by using SEQ ID Nos. 17 and 28 (using $1 \times 10^6$ RLU per reaction in both sets of assays). Ten replicate samples were assayed for each of the experimental conditions, and five replicate samples were assayed for the positive (1,000 copies) and negative (0 copies) controls and the NIBSC standard (1,000 genome equivalents/ml). The results of these tests (detected RLU mean±standard deviation) are shown in the table below.

TABLE 6

Detection of Amplified Parvovirus B19 Target Sequences Using Different Detection Probes

| Parvovirus B19 copies/ml | SEQ ID NO:17 Probe | SEQ ID NO:27 Probe | SEQ ID NO:28 Probe |
|---|---|---|---|
| 1,000 (positive control) | 273,238 ± 8,370 | 232,836 ± 7,843 | — |
|  | 269,226 ± 9,517 | — | 237,152 ± 7,482 |
| 10,000 | 282,473 ± 6,037 | 258,127 ± 16,557 | — |
|  | 288,209 ± 5,299 | — | 242,686 ± 13,025 |
| 5,000 | 283,015 ± 3,716 | 245,047 ± 5,292 | — |
|  | 282,135 ± 14,676 | — | 238,992 ± 3,790 |
| 1,000 | 263,795 ± 22,793 | 241,110 ± 7,211 | — |
|  | 261,161 ± 13,038 | — | 236,014 ± 6,581 |
| 500 | 224,858 ± 83,219 | 216,921 ± 44,803 | — |
|  | 228,023 ± 50,281 | — | 209,931 ± 49,130 |

TABLE 6-continued

Detection of Amplified Parvovirus B19 Target Sequences Using Different Detection Probes

| Parvovirus B19 copies/ml | SEQ ID NO:17 Probe | SEQ ID NO:27 Probe | SEQ ID NO:28 Probe |
|---|---|---|---|
| 250 | 167,216 ± 80,594 | 138,291 ± 53,137 | — |
|  | 158,861 ± 100,765 | — | 144,024 ± 75,550 |
| 100 | 84,296 ± 77,843 | 79,058 ± 70,042 | — |
|  | 97,111 ± 97,430 | — | 56,746 ± 42,133 |
| 50 | 39,551 ± 49,759 | 30,533 ± 47,622 | — |
|  | 58,045 ± 83,433 | — | 85,278 ± 101,652 |
| 25 | 16,403 ± 44,038 | 1,526 ± 1,700 | — |
|  | 41,375 ± 72,116 | — | 57,283 ± 91,578 |
| 0 (negative control) | 819 ± 232 | 518 ± 55 | — |
|  | 786 ± 66 | — | 512 ± 29 |
| NIBSC Standard | 157,522 ± 67,888 | 97,318 ± 47,119 | — |
|  | 199,789 ± 68,636 | — | 191,507 ± 51,276 |

The results showed that the three assay formats that used different detection probes were substantially equivalent in their reactivity and sensitivity. That is, based on a positive signal of 30,000 or more detected RLU, all three formats detected 100 copies or more of parvovirus B19 per ml of sample, and frequently detected fewer copies of parvovirus b19 (25 and/or 50 copies/ml).

EXAMPLE 8

Detection of Amplified Parvovirus B19 Sequences Using Different Detection Probes This example tested the sensitivity of the assay using individual detection probes or a mixture of two different detection probes. The mixture of detection probes contained equivalent amounts of probes of SEQ ID NO:27 and SEQ ID NO:28. Assays compared the detection probe mixture to use of either detection probe alone. The assays were performed substantially as described in Example 5, but using plasma samples that contained no parvovirus B19 (negative control), or contained 500, 250, 100, 50, or 25 copies of parvovirus B19 per ml; positive controls contained 1,000 copies/ml. Samples (1 ml) were assayed by first capturing the parvovirus B19 DNA in a hybridization complex on magnetic particles by using an oligomer having SEQ ID NO:1 with a 3' poly-A tail, as described above. Then, the parvovirus B19 target sequence was amplified by using a one-hour TMA reaction that included a promoter primer of SEQ ID NO:23 and a primer of SEQ ID NO:13. The amplification products were detected by using detection probes of either SEQ ID NO:27 or SEQ ID NO:28 individually, or a mixture of probes of SEQ ID NO:27 and SEQ ID NO:28. The probes were labeled with 2-methyl-AE (between nt 5 and 6 for SEQ ID NO:27, and nt 9/10 for SEQ ID NO:28) and used at an activity of $1 \times 10^6$ RLU per reaction for each probe. For the positive and negative controls, five replicate samples were tested, whereas for each of the other experimental conditions, twenty replicate samples were tested. The results (RLU mean±standard deviation) are shown below.

TABLE 7

Detection Results Using Labeled Probes Alone or a Mixture of Labeled Probes

| Parvovirus B19 copies/ml | SEQ ID NO:27 | SEQ ID NO:28 | SEQ ID NO:27 and SEQ ID NO:28 |
|---|---|---|---|
| 1,000 (positive control) | 464,906 ± 10,157 | 476,397 ± 8,369 | 828,543 ± 31,127 |
| 500 | 412,338 ± 95,435 | 457,938 ± 34,499 | 679,652 ± 210,438 |
| 250 | 296,947 ± 179,021 | 397,804 ± 111,879 | 554,294 ± 272,640 |
| 100 | 167,560 ± 153,175 | 262,557 ± 189,262 | 376,880 ± 254,070 |
| 50 | 95,581 ± 145,780 | 70,364 ± 140,050 | 82,840 ± 145,301 |
| 0 (negative control) | 1,046 ± 205 | 826 ± 181 | 1,051 ± 116 |

The results show that both of the probes alone and in a mixture detected parvovirus B19 at 500 copies/ml in all of the assays performed. Samples containing fewer copies of parvovirus B19 were also detected (90 to 100% for 250 copies/ml, 75 to 85% for 100 copies/ml, and 30 to 50% for 50 copies/ml). The sensitivities of the three assay formats were substantially equivalent.

EXAMPLE 9

Parvovirus B19 Detection Using Different Detection Probes

In this example, the amplified products produced using the method substantially as described in Example 8 were detected using various detection probe oligomers. The detection probe oligomers varied from one another either in their nucleotide sequence or, for probe oligomers with the same nucleotide sequence, at the position of label attachment to the oligomer. All of the probes were synthesized in vitro using standard chemical methods to produce an oligomer of specified sequence with a 2'-O-methoxy backbone. Oligomers were labeled with 2-methyl-AE as previously described (U.S. Pat. Nos. 5,585,481 and 5,639,604) using a linker compound to attach the label compound to the oligomer and used at an activity of $1 \times 10^6$ RLU per reaction. The label position on the oligomer is referred to by the adjacent nucleotide positions, e.g., "12/13" means that the linker and attached label are located between nt 12 and nt 13 of the oligomer. The detection probe oligomers tested in these experiments are summarized below.

TABLE 8

Labeled Probes

| SEQ ID NO | Nucleotide Sequence | Label Positions |
|---|---|---|
| 27 | GTCATGGACAGTTATCTGAC | 7/8, 9/10, 12/13, and 13/14 |
| 28 | GTATTATCTAGTGAAGACTTAC | 12/13 |
| 30 | CTAGTGAAGACTTACACAAGC | 5/6 and 13/14 |
| 31 | GTGAAGACTTACACAAGCCTG | 9/10 and 10/11 |
| 32 | GCAGTATTATCTAGTGAAGAC | 8/9 and 12/13 |
| 34 | CAAAGTCATGGACAGTTATCTG | 7/8, 9/10, 11/12, 13/14, 16/17, and 17/18 |
| 36 | CTGTTTGACTTAGTTGCTCG | 6/7, 7/8, 10/11, 11/12, 14/15, and 15/16 |
| 37 | CTCTCCAGACTTATATAGTCATCAT | 7/8, 8/9, 9/10, 11/12, 12/13, 14/15, 16/17, 17/18, and 18/19 |

The results of assays that used these detection probes are shown below, reported as the average (mean) RLU detected. Each probe was tested in five replicate assays of human plasma samples that contained no parvovirus B19 DNA (negative samples) and plasma that contained 1,000 copies/ml of parvovirus B19 (positive samples). The ratio of RLU detected in the positive samples to RLU detected in the negative samples (detection ratio) was determined using the average RLU results for each probe.

TABLE 9

Results Obtained By Using Different Labeled Probes

| SEQ ID NO. and Label Position | Positive Samples (mean RLU) | Negative Samples (mean RLU) | Detection Ratio |
|---|---|---|---|
| NO:27, Label 7/8 | 287,160 | 409 | 702 |
| NO:27, Label 9/10 | 419,399 | 610 | 687 |
| NO:27, Label 12/13 | 415,421 | 691 | 601 |
| NO:27, Label 13/14 | 461,686 | 747 | 618 |
| NO:28, Label 12/13 | 383,934 | 864 | 444 |
| NO:30, Label 5/6 | 432,460 | 874 | 495 |
| NO:30, Label 13/14 | 422,976 | 2,626 | 161 |
| NO:31, Label 9/10 | 413,436 | 3,107 | 133 |
| NO:31, Label 10/11 | 545,659 | 3,398 | 160 |
| NO:32, Label 8/9 | 471,379 | 864 | 545 |
| NO:32, Label 12/13 | 445,970 | 473 | 943 |
| NO:34, Label 7/8 | 535,343 | 7,105 | 75 |
| NO:34, Label 9/10 | 473,386 | 1,044 | 453 |
| NO:34, Label 11/12 | 369,158 | 647 | 570 |
| NO:34, Label 13/14 | 364,239 | 823 | 442 |
| NO:34, Label 16/17 | 220,368 | 672 | 328 |
| NO:34, Label 17/18 | 373,932 | 950 | 393 |
| NO:36, Label 6/7 | 520,799 | 814 | 639 |
| NO:36, Label 7/8 | 482,847 | 792 | 609 |
| NO:36, Label 10/11 | 370,929 | 633 | 586 |
| NQ:36, Label 11/12 | 343,754 | 757 | 454 |
| NO:36, Label 14/15 | 364,239 | 823 | 442 |
| NO:36, Label 15/16 | 382,139 | 1,016 | 376 |
| NO:37, Label 7/8 | 336,293 | 61,020 | 5 |
| NO:37, Label 8/9 | 81,986 | 1,314 | 62 |
| NO:37, Label 9/10 | 516,495 | 57,853 | 9 |
| NO:37, Label 11/12 | 559,173 | 133,530 | 4 |
| NO:37, Label 12/13 | 506,083 | 121,133 | 4 |
| NO:37, Label 14/15 | 593,889 | 54,116 | 5 |
| NO:37, Label 16/17 | 439,755 | 94,380 | 4 |
| NO:37, Label 17/18 | 361,001 | 91,163 | 4 |
| NO:37, Label 18/19 | 222,039 | 2,233 | 99 |

The results showed that a variety of different detection probes may be used to detect parvovirus B19 sequences in the amplification product because all of the probes tested produced at least four-fold more signal than the negative controls. Preferred embodiments generally have a detection ratio of 10 or greater. More preferably, the detection ratio is 100 or greater, and most preferably is in a range of 300 to 950. These results also showed that, for the same nucleotide sequence, the position of the label on the oligomer may influence the detection signal produced.

The present invention has been described in the context of particular examples and preferred embodiments. Those skilled in the art will appreciate that other embodiments are encompassed within the invention defined by the claims that follow.

We claim:

1. A combination of at least two separate nucleic acid oligomers wherein the first oligomer is selected from the group consisting of:
   a) SEQ ID NO: 24,
   b) the complete complement of SEQ ID NO: 24, and
   c) the RNA equivalent of the sequence of a) or b),
wherein the first oligomer optionally includes a promoter sequence joined to the 5' terminus of the sequence;
and wherein the second oligomer is selected from the group consisting of:
   d) SEQ ID NO: 13,
   e) the complete complement of SEQ ID NO: 13, and
   f) the RNA equivalent of the sequence of d) or e).

2. The combination of oligomers of claim 1 wherein the oligomer that consists of SEQ ID NO: 24 and a promoter sequence joined to the 5' terminus of SEQ ID NO: 24 consists of SEQ ID NO: 23.

3. The combination of oligomers of claim 1 wherein the promoter sequence joined to the 5' terminus of the sequence is the promoter sequence of SEQ ID NO: 19.

4. The combination of oligomers of claim 1, further comprising a third nucleic acid oligomer that contains a target complementary sequence of 27 to 33 nucleotides and which includes a target specific sequence consisting of a) SEQ ID NO: 41, b) the complete complement of SEQ ID NO: 41, or c) the RNA equivalent of the sequence of a) or b); and wherein the third oligomer optionally includes a 3' tail portion that is non specific for a parvovirus target sequence, and wherein the target specific sequence optionally includes at least one 2'-methoxy substituted RNA group.

5. The combination of oligomers of claim 4, wherein the third oligomer contains the target specific sequence consisting of a) SEQ ID NO: 20, b) the complete complement of SEQ ID NO: 20, or c) the RNA equivalent of the sequence of a) or b), and optionally a 3' tail portion that is non specific for a parvovirus target.

6. The combination of oligomers of claim 4 wherein the third oligomer contains the target specific sequence consisting of a) SEQ ID NO: 21, b) the complete complement of SEQ ID NO: 21, or c) the RNA equivalent of the sequence of a) or b), and optionally a 3' tail portion that is non specific for a parvovirus target.

7. The combination of oligomers of claim 4 wherein the target specific sequence of the third oligomer includes at least one 2'-methoxy substituted RNA group.

8. The combination of oligomers of claim 1, further comprising a third nucleic acid oligomer consisting of a target specific sequence of at least 25 contiguous bases contained in a) SEQ ID NO: 1, b) the complete complement of SEQ ID NO: 1, or c) the RNA equivalent of the sequence of a) or b), and optionally a 3' tail portion that is non specific for a parvovirus target sequence.

9. The combination of oligomers of claim 1, further comprising a third nucleic acid oligomer consisting of a) SEQ ID NO: 28, b) the complete complement of SEQ ID NO: 28, c) SEQ ID NO: 31, d) the complete complement of SEQ ID NO: 31, e) SEQ ID NO: 32, f) the complete complement of SEQ ID NO: 32, g) SEQ ID NO: 39, h) the complete complement of SEQ ID NO: 39, i) SEQ ID NO: 40, j) the complete complement of SEQ ID NO: 40, or k) the RNA equivalent of the sequence of any one of a)–j); wherein the third oligomer optionally includes at least one 2'-methoxy substituted RNA group.

10. The combination of oligomers of claim 9 wherein the third oligomer consists of a) the sequence of SEQ ID NO: 40, b) the complete complement of SEQ ID NO: 40, or c) the RNA equivalent of the sequence of a) or b).

11. The combination of oligomers of claim 9 wherein the third oligomer consists of a) the sequence of SEQ ID NO: 28, b) the complete complement of SEQ ID NO: 28, c) the sequence of SEQ ID NO: 32, d) the complete complement of SEQ ID NO: 32, or e) the RNA equivalent of the sequence of any one of a)–d).

12. The combination of oligomers of claim 9 wherein the third oligomer consists of a) the sequence of SEQ ID NO: 39, b) the complete complement of SEQ ID NO: 39, or c) the RNA equivalent of the sequence a) or b).

13. The combination of oligomers of claim 9 wherein the third oligomer consists of a) the sequence of SEQ ID NO: 31, b) the complete complement of SEQ ID NO: 31, or c) the RNA equivalent of the sequence of a) or b).

14. The combination of oligomers of claim 9 wherein the third oligomer includes at least one 2'-methoxy substituted RNA group.

15. A method of detecting human parvovirus B19 nucleic acid in a biological sample, comprising the steps of:
   providing a biological sample containing parvovirus B19 nucleic acid;
   amplifying in vitro a portion of the parvovirus B19 nucleic acid by using at least one nucleic acid polymerase activity and at least one first amplification oligomer and one second amplification oligomer, selected from the group consisting of
  a first amplification oligomer consisting of SEQ ID NO:23 or SEQ ID NO:24 optionally including a promoter sequence joined to a 5' terminus of SEQ ID NO:24, and
  a second amplification oligomer consisting of SEQ ID NO:13; and
detecting an amplified product of the parvovirus B19 nucleic acid by using a labeled detection probe that hybridizes specifically with the amplified product, thereby indicating presence of parvovirus B19 nucleic acid in the biological sample.

16. The method of claim 15, wherein the amplifying step uses the oligomer consisting of SEQ ID NO: 24 including a promoter sequence joined to the 5' terminus of SEQ ID NO: 24, and the oligomer consisting of the sequence of SEQ ID NO: 13.

17. The method of claim 15, wherein the amplifying step uses an amplification reaction that is substantially isothermal.

18. The method of claim 15, wherein the detecting step uses a labeled detection probe selected from the group consisting of SEQ ID NO:28, SEQ ID NO:31, SEQ ID NO:32, SEQ ID NO:39, and SEQ ID NO:40.

19. The method of claim 15, wherein the detecting step uses a labeled detection probe consisting of SEQ ID NO:28.

20. The method of claim 15, wherein the detecting step uses a labeled detection probe comprising at least one 2'-methoxy substituted RNA group.

21. The method of claim 15, wherein the detecting step uses a labeled detection probe that includes a label that is detected in a homogeneous reaction.

22. The method of claim 15, wherein the detecting step uses a labeled detection probe that includes a chemiluminescent label attached to the oligomer via a linker compound.

23. The method of claim 15, further comprising the steps of:
  contacting the biological sample with at least one capture oligomer comprising a target-specific sequence that hybridizes to a parvovirus B19 target sequence, thus forming a complex comprising the capture oligomer and parvovirus B19 nucleic acid; and
  separating the complex from the biological sample before the amplifying step.

24. The method of claim 23, wherein the capture oligomer contains a target complementary sequence of 27 to 33 nucleotides that contains a target specific sequence consisting of a) SEQ ID NO: 41, b) SEQ ID NO: 20, c) SEQ ID NO: 21, or d) the RNA equivalent of the sequence of any one of a)–c), and wherein the capture oligomer optionally includes a 3' tail sequence that is non specific for a parvovirus target sequence.

25. The method of claim 23, wherein the capture oligomer comprises at least one 2'-methoxy substituted RNA group.

* * * * *

SEQUENCE LISTING

```
<160> NUMBER OF SEQ ID NOS: 41

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence:
      synthetic construct

<400> SEQUENCE: 1
gttggctata cctaaagtca tgaatcct                                          28

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence:
      synthetic construct

<400> SEQUENCE: 2
gccagttggc tatacctaaa gtcatgaatc ct                                     32

<210> SEQ ID NO 3
<211> LENGTH: 53
<212> TYPE: DNA
<213> ORGANISM: Artificial Sequence
<220> FEATURE:
<223> OTHER INFORMATION: Description of Artificial Sequence:
      synthetic construct
<220> FEATURE:
<221> NAME/KEY: promoter
<222> LOCATION: (1)..(27)
<223> OTHER INFORMATION: T7 RNA polymerase promoter

<400> SEQUENCE: 3
aatttaatac gactcactat agggagacta ggttctgcat gactgctact gga             53

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence:
      synthetic construct

<400> SEQUENCE: 4
ctaggttctg catgactgct actgga                                            26

<210> SEQ ID NO 5
<211> LENGTH: 53
<212> TYPE: DNA
<213> ORGANISM: Artificial Sequence
<220> FEATURE:
<223> OTHER INFORMATION: Description of Artificial Sequence:
      synthetic construct
<220> FEATURE:
<221> NAME/KEY: promoter
<222> LOCATION: (1)..(27)
<223> OTHER INFORMATION: T7 RNA polymerase promoter
```

```
<400> SEQUENCE: 5
aatttaatac gactcactat agggagactg catgactgct actggatgat aag        53

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence:
      synthetic construct

<400> SEQUENCE: 6
ctgcatgact gctactggat gataag                                      26

<210> SEQ ID NO 7
<211> LENGTH: 56
<212> TYPE: DNA
<213> ORGANISM: Artificial Sequence
<220> FEATURE:
<223> OTHER INFORMATION: Description of Artificial Sequence:
      synthetic construct
<220> FEATURE:
<221> NAME/KEY: promoter
<222> LOCATION: (1)..(27)
<223> OTHER INFORMATION: T7 RNA polymerase promoter

<400> SEQUENCE: 7
aatttaatac gactcactat agggagacta ggttctgcat gactgctact ggatga     56

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence:
      synthetic construct

<400> SEQUENCE: 8
ctaggttctg catgactgct actggatga                                   29

<210> SEQ ID NO 9
<211> LENGTH: 52
<212> TYPE: DNA
<213> ORGANISM: Artificial Sequence
<220> FEATURE:
<223> OTHER INFORMATION: Description of Artificial Sequence:
      synthetic construct
<220> FEATURE:
<221> NAME/KEY: promoter
<222> LOCATION: (1)..(27)
<223> OTHER INFORMATION: T7 RNA polymerase promoter

<400> SEQUENCE: 9
aatttaatac gactcactat agggagagtt ctgcatgact gctactggat ga         52

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence:
      synthetic construct

<400> SEQUENCE: 10
gttctgcatg actgctactg gatga                                       25
```

<210> SEQ ID NO 11
<211> LENGTH: 53
<212> TYPE: DNA
<213> ORGANISM: Artificial Sequence
<220> FEATURE:
<223> OTHER INFORMATION: Description of Artificial Sequence:
     synthetic construct
<220> FEATURE:
<221> NAME/KEY: promoter
<222> LOCATION: (1)..(27)
<223> OTHER INFORMATION: T7 RNA polymerase promoter

<400> SEQUENCE: 11
aatttaatac gactcactat agggagattc tcctctaggt tctgcatgac tgc                53

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence:
     synthetic construct

<400> SEQUENCE: 12
ttctcctcta ggttctgcat gactgc                                              26

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:
     synthetic construct

<400> SEQUENCE: 13
cccctagaaa acccatcctc t                                                   21

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence:
     synthetic construct

<400> SEQUENCE: 14
ctctccagac ttatatagtc atcattttc                                           29

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence:
     synthetic construct

<400> SEQUENCE: 15
ctctccagac ttatatagtc atcat                                               25

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence:
     synthetic construct

<400> SEQUENCE: 16

```
atcccctaga aaacccatcc tct                                    23

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence:
      synthetic construct

<400> SEQUENCE: 17
gacagttatc tgaccacccc catgc                                  25

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence:
      synthetic construct

<400> SEQUENCE: 18
catggacagt tatctgacca cc                                     22

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence:
      synthetic construct

<400> SEQUENCE: 19
aatttaatac gactcactat agggaga                                27

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence:
      synthetic construct

<400> SEQUENCE: 20
catcactttc ccaccatttg ccacttt                                27

<210> SEQ ID NO 21
<211> LENGTH: 32
<212> TYPE: DNA
<213> ORGANISM: Artificial Sequence
<220> FEATURE:
<223> OTHER INFORMATION: Description of Artificial Sequence:
      synthetic construct

<400> SEQUENCE: 21
gcaaatttat catcactttc ccaccatttg cc                          32

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence:
      synthetic construct

<400> SEQUENCE: 22
aggattcatg actttaggta tagccaac                               28
```

```
<210> SEQ ID NO 23
<211> LENGTH: 52
<212> TYPE: DNA
<213> ORGANISM: Artificial Sequence
<220> FEATURE:
<223> OTHER INFORMATION: Description of Artificial Sequence:
      synthetic construct
<220> FEATURE:
<221> NAME/KEY: promoter
<222> LOCATION: (1)..(27)
<223> OTHER INFORMATION: T7 RNA polymerase promoter

<400> SEQUENCE: 23
aatttaatac gactcactat agggagaagt accgggtagt tgtacgctaa ct            52

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence:
      synthetic construct

<400> SEQUENCE: 24
agtaccgggt agttgtacgc taact                                          25

<210> SEQ ID NO 25
<211> LENGTH: 53
<212> TYPE: DNA
<213> ORGANISM: Artificial Sequence
<220> FEATURE:
<223> OTHER INFORMATION: Description of Artificial Sequence:
      synthetic construct
<220> FEATURE:
<221> NAME/KEY: promoter
<222> LOCATION: (1)..(27)
<223> OTHER INFORMATION: T7 RNA polymerase promoter

<400> SEQUENCE: 25
aatttaatac gactcactat agggagacta ggttctgcat gactgctact gga           53

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence:
      synthetic construct

<400> SEQUENCE: 26
ctaggttctg catgactgct actgga                                         26

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence:
      synthetic construct

<400> SEQUENCE: 27
gtcatggaca gttatctgac                                                20

<210> SEQ ID NO 28
<211> LENGTH: 22
<212> TYPE: DNA
<213> ORGANISM: Artificial Sequence
```

```
<220> FEATURE:
<223> OTHER INFORMATION: Description of Artificial Sequence:
      synthetic construct

<400> SEQUENCE: 28
gtattatcta gtgaagactt ac                                           22

<210> SEQ ID NO 29
<211> LENGTH: 37
<212> TYPE: DNA
<213> ORGANISM: Artificial Sequence
<220> FEATURE:
<223> OTHER INFORMATION: Description of Artificial Sequence:
      synthetic construct

<400> SEQUENCE: 29
aaagtggcaa atggtgggaa agtgatgata aatttgc                           37

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence:
      synthetic construct

<400> SEQUENCE: 30
ctagtgaaga cttacacaag c                                            21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence:
      synthetic construct

<400> SEQUENCE: 31
gtgaagactt acacaagcct g                                            21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence:
      synthetic construct

<400> SEQUENCE: 32
gcagtattat ctagtgaaga c                                            21

<210> SEQ ID NO 33
<211> LENGTH: 34
<212> TYPE: DNA
<213> ORGANISM: Artificial Sequence
<220> FEATURE:
<223> OTHER INFORMATION: Description of Artificial Sequence:
      synthetic construct

<400> SEQUENCE: 33
gcagtattat ctagtgaaga cttacacaag cctg                              34

<210> SEQ ID NO 34
<211> LENGTH: 22
<212> TYPE: DNA
<213> ORGANISM: Artificial Sequence
<220> FEATURE:
```

<223> OTHER INFORMATION: Description of Artificial Sequence:
      synthetic construct

<400> SEQUENCE: 34
caaagtcatg gacagttatc tg                                             22

<210> SEQ ID NO 35
<211> LENGTH: 35
<212> TYPE: DNA
<213> ORGANISM: Artificial Sequence
<220> FEATURE:
<223> OTHER INFORMATION: Description of Artificial Sequence:
      synthetic construct

<400> SEQUENCE: 35
caaagtcatg gacagttatc tgaccacccc catgc                               35

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence:
      synthetic construct

<400> SEQUENCE: 36
ctgtttgact tagttgctcg                                                20

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence:
      synthetic construct

<400> SEQUENCE: 37
ctctccagac ttatatagtc atcat                                          25

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence:
      synthetic construct

<400> SEQUENCE: 38
gtcatggaca gttatctg                                                  18

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence:
      synthetic construct

<400> SEQUENCE: 39
gtgaagactt acacaagc                                                  18

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence:

-continued

```
synthetic construct

<400> SEQUENCE: 40
gtattatcta gtgaagac                                              18

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence:
      synthetic construct

<400> SEQUENCE: 41
catcactttc ccaccatttg cc                                         22
```